United States Patent [19]
De Smet et al.

[11] Patent Number: 6,027,922
[45] Date of Patent: *Feb. 22, 2000

[54] HUMAN FOAM CELLS AND METHODS FOR PREPARING THEM, MONOCLONAL ANTIBODIES TO SAID FOAM CELLS AND THEIR PHARMACEUTICAL AND DIAGNOSTIC USE

[75] Inventors: Walter De Smet, Aalst; Ann Union, Aalter, both of Belgium

[73] Assignee: Innogenetics N.V., Ghent, Belgium

[*] Notice: This patent issued on a continued prosecution application filed under 37 CFR 1.53(d), and is subject to the twenty year patent term provisions of 35 U.S.C. 154(a)(2).

[21] Appl. No.: 08/637,669

[22] PCT Filed: Oct. 26, 1994

[86] PCT No.: PCT/EP94/03514

§ 371 Date: May 2, 1996

§ 102(e) Date: May 2, 1996

[87] PCT Pub. No.: WO95/12666

PCT Pub. Date: May 11, 1995

[30] Foreign Application Priority Data

Nov. 2, 1993 [EP] European Pat. Off. ............. 93402691

[51] Int. Cl.$^7$ .................. C07K 16/28; C07K 16/30; C07N 5/12; C07N 5/02

[52] U.S. Cl. ............. 435/70.21; 435/70.2; 435/332.334; 435/343; 435/344; 436/548; 530/387.1; 530/387.3; 530/387.22; 530/388.7; 530/809; 530/388.8

[58] Field of Search ............... 424/133.1, 143.1, 424/152.1, 172.1, 178.1, 809; 435/2, 70.2, 70.21, 240.27, 89, 104, 106, 107, 334; 530/387.1, 387.3, 388.22, 388.7, 389.6, 391.1, 391.3, 388.8, 809; 436/548; 432/332, 343, 344

[56] References Cited

FOREIGN PATENT DOCUMENTS

90/05748 5/1990 WIPO.
92/22323 12/1992 WIPO.
93/14776 5/1993 WIPO.

OTHER PUBLICATIONS

Harris et al., TIBTECH, 11:42–44, 1993.
Waldmann, Science, 252:1657–1662, 1991.
ATCC Cell lines and hybridomal catalogue, 8th Edition, 1994, pp. 339, XV and XVI.
Borrebaeck et al., Imm. Today, 14: 477–479, 1993.
Schlossman et al., "Leucocyte Typing V, White Cell Differentiation Antigens, Proceedings of the Fifth Int. Workshop and Conference Held in Boston, USA Nov. 3–7, 1993". Oxford Univ. Press, 1995 pp. 1457–1467.
Hani et al., Arth. and Rheuma., 37:846–854, 1994 (Abstract thereof).
Springer et al., "AS1 Adhesion structutes: section report", from "Leucocyte Typing V" ed. Schlossman et al., Oxford Univ. Press, 1995, pp. 1443–1447.
Tissue Antigens, vol. 42, No. 4, Oct. 1993, Copenhagen, p. 412, Union et al, 'Up–regulation of the CD36 and Cdw17 antigen on "in vitro" human foam cells'.
Journal of Biological Chemistry, vol. 268, No. 16, Jun. 5, 1993, Baltimore, Md., U.S., pp. 11811 011816, Endemann, G. Et al 'CD36 is a receptor for oxidized low density lipoprotein'.
Biochemistry vol. 27, 1988, Easton, Pa., U.S., pp. 2651–2655, Auwerx, J. H. Et al 'transcriptional activation of the lipoprotein lipase and apolipoprotein E genes accompanies differentiation in some human macrophage–like cells'.

Primary Examiner—Ronald B. Schwadron
Attorney, Agent, or Firm—Nixon & Vanderhye P.C.

[57] ABSTRACT

The present invention relates to human foam cells generated in vitro from monocyte/macrophage related cell lines which give rise to an average intracellular cholesterol amount of at least 139+36 ug/mg cell protein as determined by HPLC, with said cholesterol being characterized by a degree of 46+6% of esterification as determined by HPLC. The invention also relates to monoclonal antibodies selected via said foam cells and which can be used for pharmaceutical and diagnostic purposes.

2 Claims, 8 Drawing Sheets

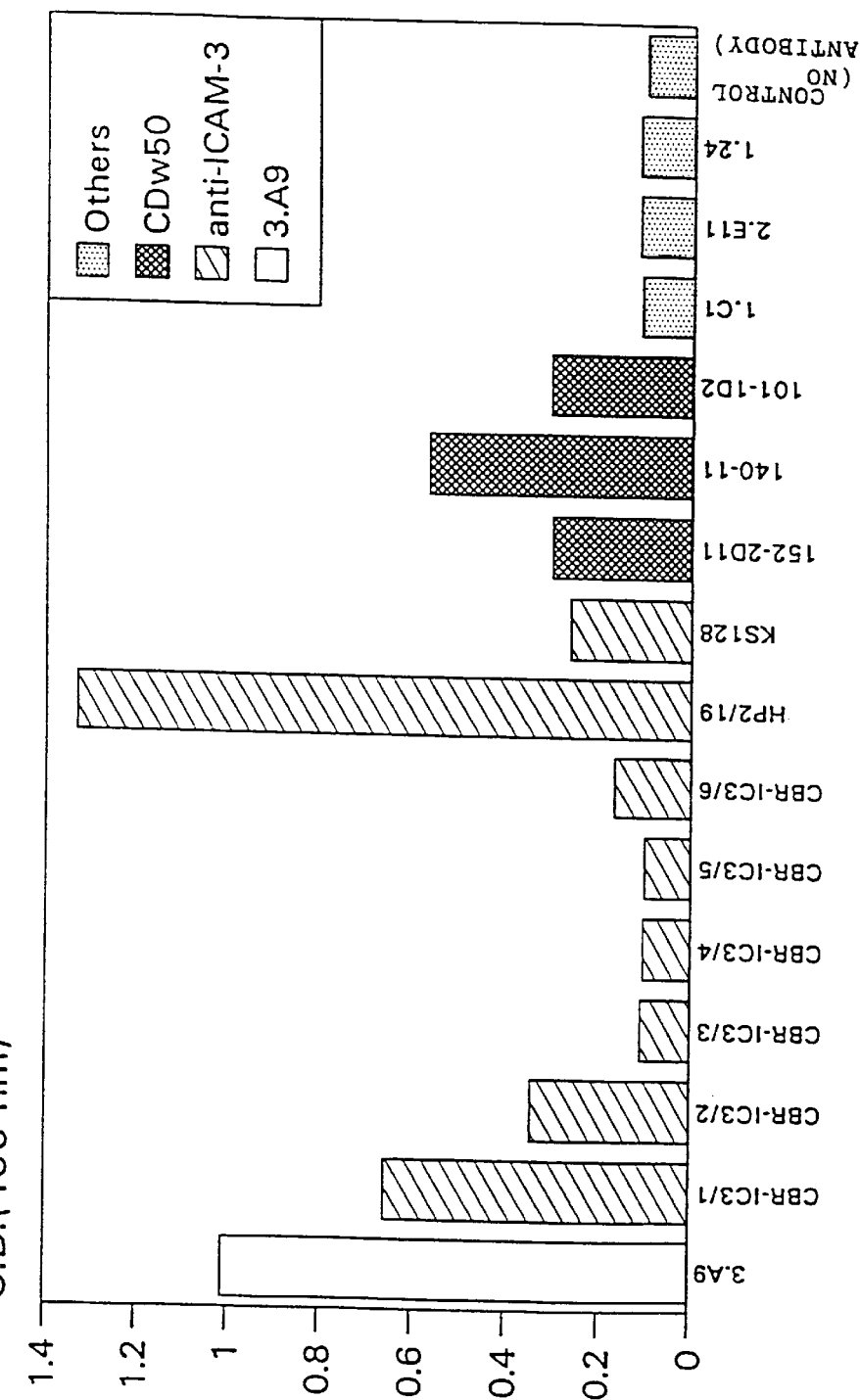

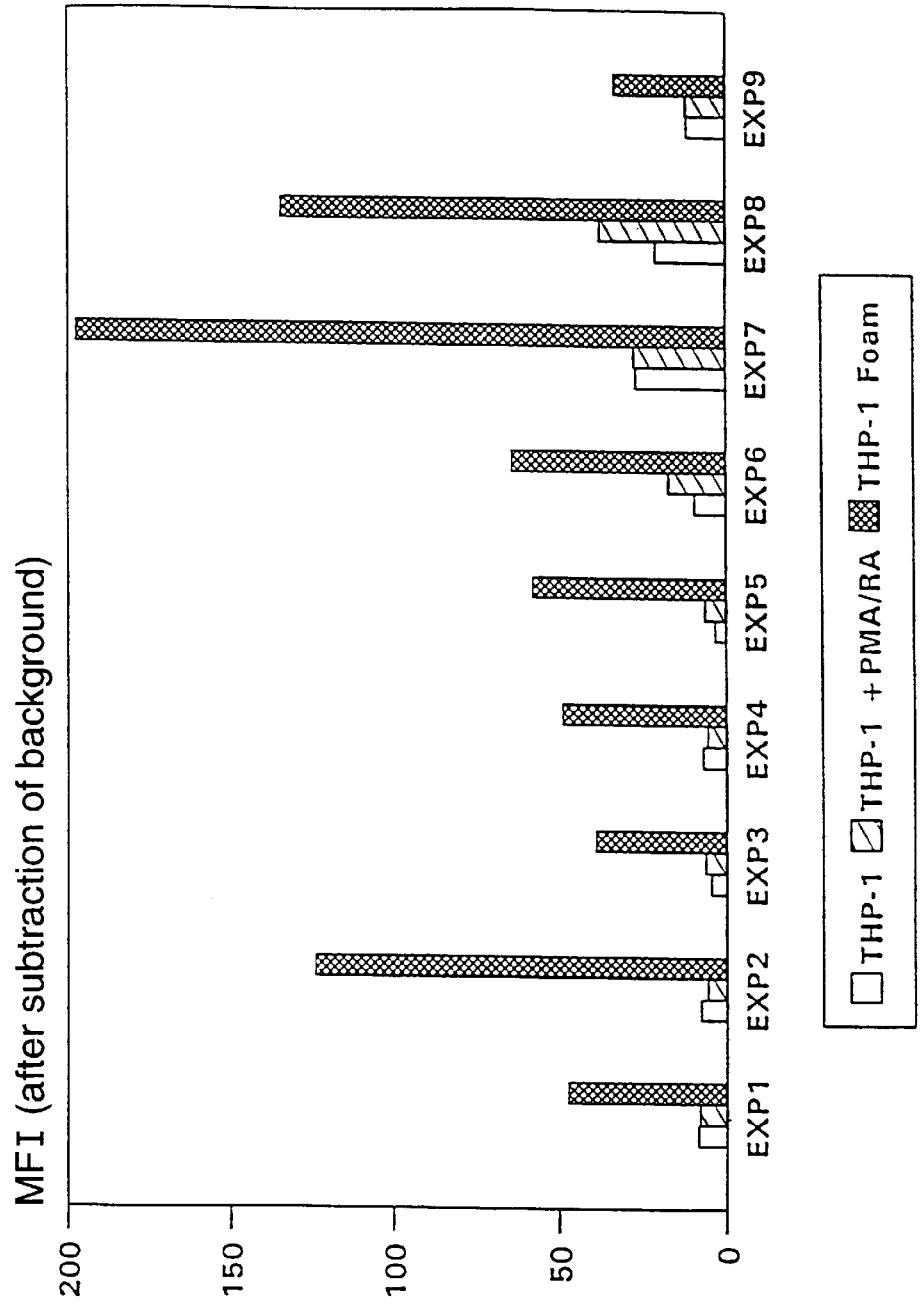

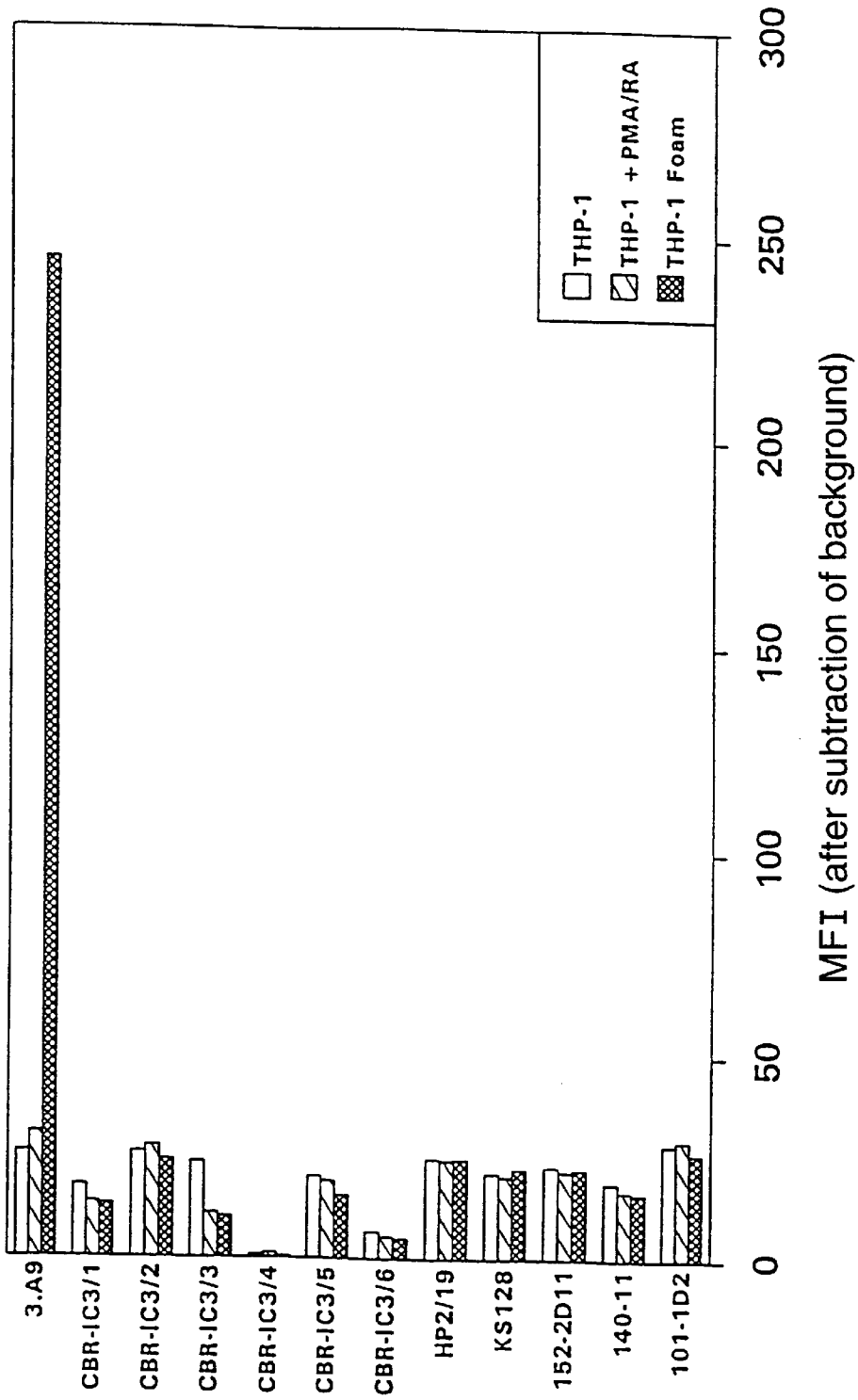

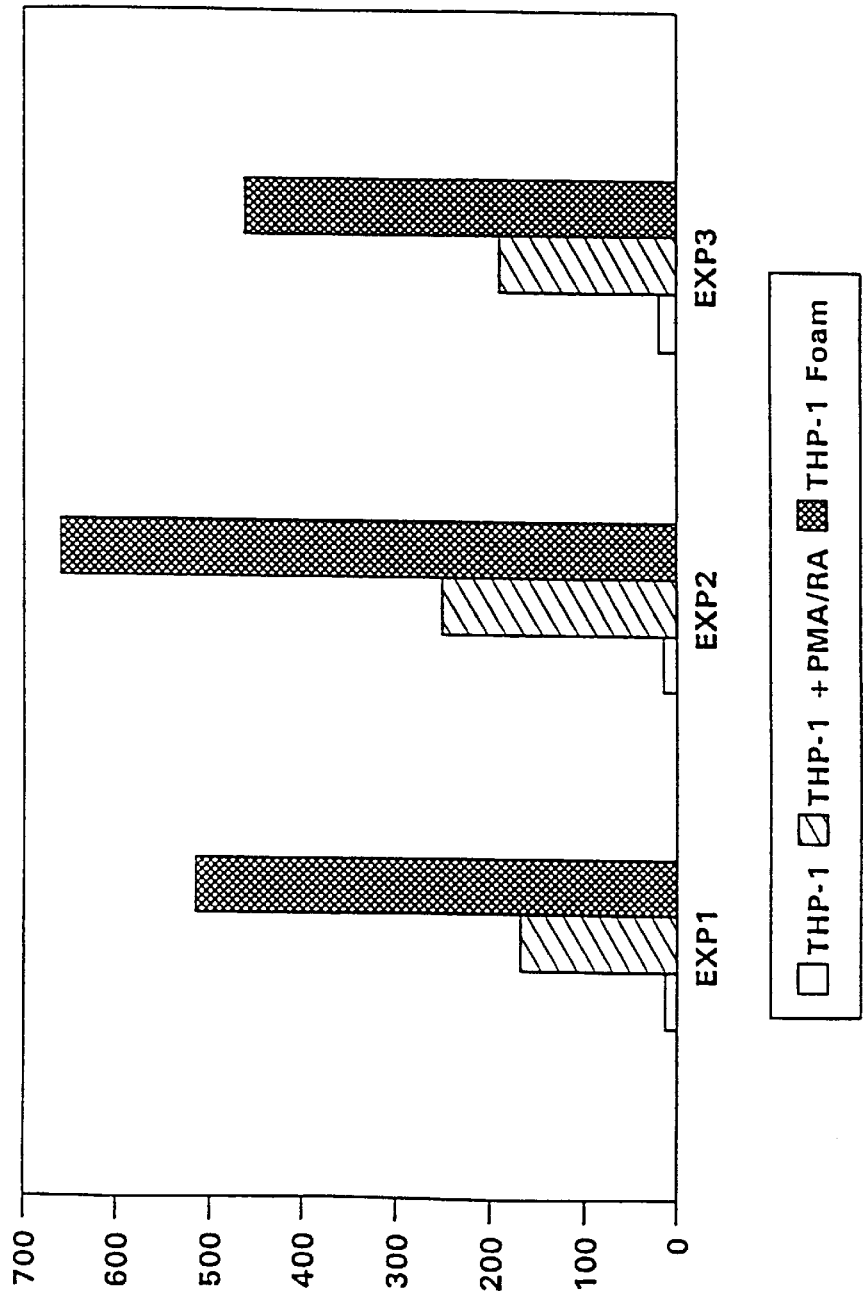

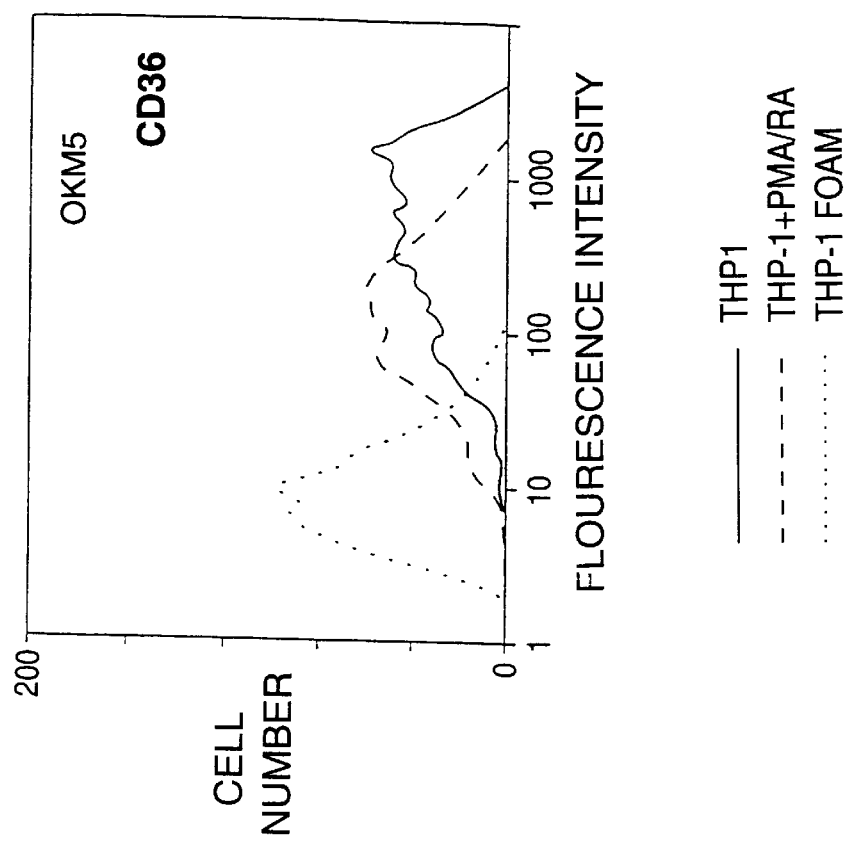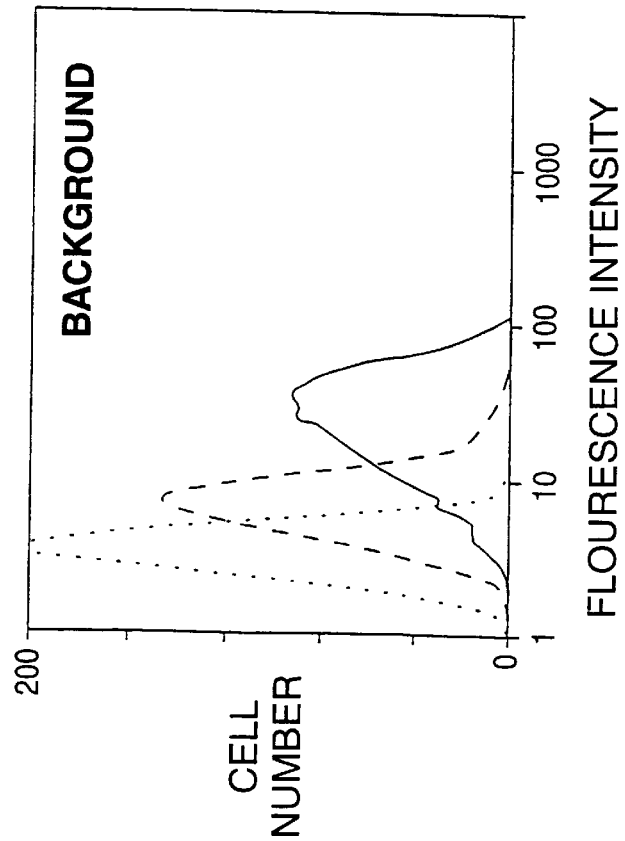

HUMAN FOAM CELLS AND METHODS FOR PREPARING THEM, MONOCLONAL ANTIBODIES TO SAID FOAM CELLS AND THEIR PHARMACEUTICAL AND DIAGNOSTIC USE

The present invention relates to new in vitro generated human foam cells, the method for preparing the same, the use of said foam cells in an in vitro method for selecting specific compounds, more particularly monoclonal antibodies found to recognize specifically ICAM-3, a process for preparing the monoclonal antibodies according to the invention, and their use for pharmaceutical and diagnostic purposes.

Atherosclerosis involves a combination of changes in the intima of the arterial wall, resulting in thickening and hardening of the arteries; typical lesions such as fatty streaks and fibrous plaques consisting of lipids, proteins and other components become calcified fibrous plaques which affect the underlying media at later stages. The disease originates from a response to an injury of the endothelial cells and has a lot of properties in common with inflammatory processes in other tissues (Ross, 1986).

Key elements of the atherosclerotic plaque are the foam cells, which are mainly derived from circulating blood monocytes. Upon entering the arterial wall, monocytes differentiate into macrophages that avidly take up large amounts of modified lipoproteins, hence resulting in foam cell formation. The injuries of the arterial lumen lead to occluded blood flow and ultimately to clinical complications such as myocard infarct, stroke, thrombosis, angina, renal hypertension and peripheral vessel diseases.

Early detection of atherosclerotic plaques is of primarily importance to allow a timely intervention to reduce plaque size and formation and to prevent new plaque formation. Arteriography is conventionally used for diagnosing advanced vascular diseases. Because of the risks resulting from this catheterization procedure, arteriography is only performed on patients with advanced or acute atherosclerotic disease. Until now, no diagnostic methods exist that permit an early detection of atherosclerotic plaques, and there is a need for better non-invasive techniques and reagents capable of detecting, mapping and treating early, non-stenosing, non-flow-disturbing arterial lesions.

Kodama et al. (WO 90/05748) have characterized a scavenger receptor molecule and antibodies against this receptor for the detection and treatment of atherosclerosis. It concerns a receptor protein of about 220 kDa that binds acetylated and oxidized LDL. In order to isolate this receptor PMA differentiated THP-1 cells were used.

Multiple models for the generation of in vitro foam cells are already described for murine cell lines, where one of the classical systems consists of incubating murine J774A.1 cells with acetylated low density lipoproteins (LDL) for 48 hours, resulting in an intracellular cholesterol content of >100 µg/mg cell protein and a degree of esterification of +50% (Tabas et al., 1985; Via et al., 1985; Snow et al., 1988; 1992). In contrast, human macrophage-like cell lines HL-60 and U-937 could not be transformed into foam cells using acetylated-LDL (Via et al., 1985). Previous induction with phorbol 12-myristate 13-acetate (PMA) or conditioned medium of concanavalin A-stimulated lymphocytes did not influence their acetyl-LDL metabolism. The human monocytic cell line THP-1 (Tsuchiya et al., 1980) could be induced by PMA to a differentiated phenotype expressing numerous functional macrophage characteristics (Tsuchiya et al., 1982). The suspension cells became growth arrested and adherent to the substrate, and secreted lipoprotein lipase and apolipoprotein E (Tajima et al., 1985; Auwerx et al., 1988; Menju et al., 1989). Hara et al. (1987) described an increased degradation of acetyl-LDL in PMA-differentiated THP-1 cells, even though a total cholesterol accumulation of +45 µg/mg cell protein after 48 hours is rather low in comparison to the observed cholesterol content of foam cells isolated from the atherosclerotic plaque, which normally ranges up to 300 µg/mg protein (Haley et al., 1977; St. Clair, 1986). Also, in a study of Yamamoto et al. (1988) involving PMA-induced human THP-1 and UE-12 cells, generated foam cells did only contain 20–40 µg cholesterol/mg protein.

Therefore a persistent need exists for the establishment of an in vitro human macrophage foam cell model that resembles atherosclerotic plaque foam cells with respect to their massive amounts of intracellular cholesterol and cholesteryl esters.

Several classes of leucocyte-endothelial adhesion molecules are probably involved in atherogenesis. For example, preceding their emigration into extravascular tissue, monocytes/macrophages adhere to vascular endothelial cells. This adherence is dependent on interactions between cell surface structures ("ligand-receptor" pairs) on both cell types. For the monocyte/macrophage, these are, among others, "lymphocyte function-associated antigen-1" (LFA-1), Mac-1 and/or p150,95. For the endothelial cell, these are, among others, "intercellular adhesion molecule-1" (ICAM-1) and ICAM-2.

LFA-1, Mac-1 and p150,95 (referred to in "World Health Organization" nomenclature as CD11a/CD18, CD11b/CD18 and CD11c/CD18 antigens respectively) are members of the beta 2 integrin subfamily (=leucointegrin subfamily). All three are non-covalently associated alfa-beta membrane glycoproteins. They share the same beta subunit but have distinct alfa subunits. The expression of LFA-1 is not limited to monocytes/macrophages, as it is also present on B lymphocytes, T lymphocytes and granulocytes. Although LFA-1 was originally identified by monoclonal antibodies (mAb) that inhibit T cell-mediated killing, it was later shown to participate via its interactions with its ligands ICAM-1 and -2 in a broad range of other leucocyte functions (including T-helper and B lymphocyte responses, natural killing, antibody-dependent cytotoxicity mediated by monocytes and granulocytes, and, as mentioned above, adherence of leucocytes to endothelial cells, fibroblasts and epithelial cells). For a general overview on the "leucointegrins", see Larson and Springer (1990) and Springer (1990).

ICAM-1 and ICAM-2 are both members of another family of adhesion molecules, namely the immunoglobulin gene superfamily. ICAM-1 (also called CD54 antigen) is a single chain glycoprotein varying in mass from 76 to 114 kilodalton depending on the source of cell type. It is highly inducible on a wide range of cell types with cytokines such as tumor necrosis factor, gamma-interferon and interleukin-1 (Dustin et al., 1988). ICAM-2 differs from ICAM-1 in cell distribution (see below) and cytokine induction. Based on the existence of an ICAM-1 and ICAM-2-independent pathway of adhesion to purified LFA-1, a third ligand (=ICAM-3) for LFA-1 was postulated (de Fougerolles et al., 1991) and characterized with monoclonal antibody CBR-IC3/1 (WO 92/22323; de Fougerolles and Springer, 1992). Recently, three research groups have independently described a cDNA sequence for ICAM-3 (WO 93/14776; Fawcett et al., 1992; Vazeux et al., 1992; de Fougerolles et al., 1993). Even more recently, immunochemical, functional and protein sequencing studies have shown that ICAM-3 and CDw50 antigen are the same molecule (Juan et al., 1993). CDw50 was originally defined by two mAb (101-1D2 and 140-11) and was one of the new clusters of differentiation assigned during the "Fourth International Workshop on Human Leucocyte Differentiation Antigens" (Hadam et al., 1990).

The existence of three LFA-1 ligands suggests specialisation for different aspects of LFA-1-dependent leucocyte interactions (WO 92/22323). ICAM-1 is basally expressed on endothelium and many epithelial cell types, and is strongly induced in inflammation and immunity where it regulates cell localization and facilitates specific antigen recognition (Wawryk et al., 1989). Since ICAM-2 is the predominant LFA-1 ligand on resting endothelium, this pathway of adhesion may have important consequences for normal recirculation of LFA-1 bearing lymphocytes through tissue endothelium. The finding that: (a) adhesion of resting T lymphocytes to purified LFA-1 occurs primarily via ICAM-3 (de Fougerolles and Springer, 1992); (b) the highest expression of ICAM-3 messenger RNA is found in cell types implicated in antigen presentation to T cells (namely B cells and monocytes/macrophages) (Fawcett et al., 1992; Vazeux et al., 1992); and (c) ICAM-3 is much better expressed than the other LFA-1 ligands on resting monocytes and lymphocytes (de Fougerolles and Springer, 1992) implies an important role for ICAM-3 in the initiation of immune responses. In support of this hypothesis is the finding that CDw50 mAb are capable of partially inhibiting primary allogeneic responses (Vilella et al., 1990).

The aim of the present invention is to generate novel in vitro human foam cells having a higher intracellular cholesterol content than any other in vitro generated human foam cells known in the art.

Another aim of the present invention is to provide a method for in vitro production of said human foam cells.

Another aim of the present invention is to provide foam cell markers that can be used for the early detection of atherosclerosis and other related vascular diseases.

Another aim of the present invention is to provide molecules which are specifically up-regulated in the in vitro human foam cells of the present invention.

Another aim of the present invention is to provide a drug screening system.

Another aim of the present invention is to provide a novel anti-ICAM-3 monoclonal antibody, capable of differentiating foam cells from activated non-foam cells.

Another aim of the present invention is to provide a peptide binding to said monoclonal antibody.

Another aim of the present invention is to provide a method for producing said monoclonal antibodies.

Another aim of the present invention is to provide hybridoma cell lines producing said monoclonal antibodies.

Another aim of the present invention is to provide pharmaceutical as well as diagnostic uses for said monoclonal antibodies.

All of these aims are achieved by the embodiments of the invention.

The present invention relates more particularly to human foam cells generated in vitro from monocyte/macrophage related cell lines which give rise to an average intracellular cholesterol amount of at least 139+36 $\mu$g/mg cell protein as determined by HPLC, with said cholesterol being characterized by a degree of 46+6% of esterification as determined by HPLC.

The term "foam cells" refers to lipid-loaded cells generally referred to in the art as foam cells and appearing for instance in atherosclerotic plaques (for review of foam cells see Bowyer & Mitchinson, 1989).

The term "monocyte/macrophage related cell lines" is reviewed by Lyons & Aschmann (1989) and for instance includes THP-1 cell lines.

The term "cholesteryl ester" refers to any esterified form of cholesterol.

The amount of cholesterol and cholesteryl esters may be determined by reversed phase HPLC (Vercaemst et al., 1989) as described in the Examples section. Amounts determined by any other means known in the art may be verified according to the techniques presented in the Examples section of the present invention.

The expression "molecules which are specifically up-regulated in the in vitro foam cells of the present invention" refers to compounds or molecules which show a higher binding to the "THP-1 foam cells" of the present invention than to "THP-1+PMA/RA cells" as defined in the present invention.

As presented in the Examples section, the present invention involves a new type of in vitro generated human foam cells characterized by its high amounts of intracellular cholesterol and cholesteryl esters. Such high amounts of intracellular cholesterol have never been obtained heretofore for human monocyte/macrophage related cell lines and have the advantage of resembling more the in vivo atherosclerotic plaque foam cells with respect to their massive amounts of cholesterol and cholesteryl esters.

According to another embodiment, the present invention relates to human foam cells as defined above, such as prepared from THP-1 cells activated for 24 hours with a mixture of $2 \times 10^{-7}$M phorbol 12-myristate 13-acetate (PMA) and $0.5 \times 10^{-7}$M retinoic acid (RA), and afterwards cultured for 48 hours in the presence of aggregated low density lipoprotein (LDL) (THP-1 foam).

THP-1 cells are available from the American Type Culture Collection (ATCC), 12301 Parklawn Drive, Rockville, Md. 20852-1776, U.S.A. (ATCC TIB 202, deposited Oct. 1, 1983).

The term "activated" or differentiated is reviewed by Dougherty & McBride (1989).

The term "aggregated LDL" refers to larger LDL particles which may be obtained as described in the Examples section (sonication) of the present invention or by any other technique known in the art, such as vortex mixing (Khoo et al., 1988), phospholipase C modification (Suits et al., 1989). The degree of aggregation is monitored upon preparation as described in the Examples section or by any other technique known in the art. The preferred concentration of aggregated LDL in the medium as disclosed in the Examples section is 200 $\mu$g/ml. The preferred growing conditions for generating THP-1 derived foam cells are extensively depicted in the Examples section. It is, however, to be understood that any modifications known to the skilled man may be introduced which would increase in THP-1 cells the uptake of native LDL or any modified LDL known in the art.

Other monocyte/macrophage related cell lines besides THP-1 might also be suited to generate foam cells having the above-mentioned characteristics and following the above-outlined protocols. Up till now, such cell lines have not been characterized.

The Example section of the present invention demonstrates that THP-1 cells grown under the therein specified conditions contain remarkably high intracellular cholesterol amounts as specified above. The human foam cells of the invention being defined as containing an average intracellular cholesterol amount of at least 139+36 $\mu$g/mg cell protein of which 46+6% is in the esterified form, and being obtained by activating THP-1 cells for 24 hours with a mixture of $2\times10^{-7}$M phorbol 12-myristate 13-acetate (PMA) and $0.5\times10^{-7}$M retinoic acid (RA), and afterwards culturing them for 48 hours in medium with aggregated low density lipoprotein will further be referred to as "THP-1 foam" cells.

According to a preferred embodiment, the present invention relates to the use of human foam cells as defined above for selecting compounds which show an increased binding to human foam cells (THP-1 foam) as defined above compared to their binding to human cells prepared by activating THP-1 cells for 24 hours with a mixture of $2\times10^{-7}$M phorbol 12-myristate 13-acetate (PMA) and $0.5\times10^{-7}$M retinoic acid (RA), and afterwards culturing them for 48 hours under lipid-free conditions (THP-1+PMA/RA).

As demonstrated in the Examples section, certain compounds may be found which show a higher binding to THP-1 foam cells than THP-1 cells activated for 24 hours with a mixture of $2\times10^{-7}$M phorbol 12-myristate 13-acetate (PMA) and $0.5\times10^{-7}$M retinoic acid (RA), and afterwards culturing them for 48 hours under lipid-free conditions (referred to as THP-1+PMA/RA).

The "increased binding" may be determined by indirect immunofluorescence such as analyzed by flow cytometry (FACS analysis) or by any other technique known by the man skilled in the art, such as immuno-labelling or enzyme-labelling techniques. The term "increased binding" refers to at least 2 times, preferably 3 times, and even more preferably at least 5 times the binding observed for the same compound to THP-1+PMA/RA cells.

The term "compounds" refers to any type of molecule such as antibodies, peptides, drugs, etc., preferably however a monoclonal antibody. Such compounds may be of interest to diagnose the presence of foam cells (for instance in atherosclerotic plaques) or to inhibit the formation of such foam cells by inhibiting their uptake of LDL. The THP-1 foam cell model may be used for testing new or known molecules, chemical and pharmaceutical compounds with respect to their inhibitory capacity for lipoprotein uptake and cholesterol accumulation, thereby preventing foam cell formation. The human in vitro foam cell model of the present invention is thus also to be used for screening new or known peptides and proteins, and complexes thereof acting as cholesterol acceptors and carriers that provide cholesterol efflux from lipid-loaden cells, which can be used for the removal of cholesterol from atherosclerotic lesions.

In the examples section of the present invention several examples are given by way of illustration of how the human foam cell system of the present invention can be used to select specific antibodies which show an increased binding to THP-1 foam cells compared to THP-1+PMA/RA cells as determined by indirect immunofluorescence and which are potentially interesting as foam cell markers (such for instance as atherosclerotic prognostic markers).

As used herein, the term "antibody" refers to polyclonal antibodies, monoclonal antibodies, humanized antibodies, single-chain antibodies, and fragments thereof such as F(ab), F(ab')2, Fv, and other fragments which retain the antigen binding function of the parent antibody.

Particularly preferred examples of compounds according to this embodiment of the invention are monoclonal antibodies. The term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as F(ab), F(ab')2, Fv, and others which retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

According to a preferred embodiment, the present invention relates to a monoclonal antibody characterized as showing an increased binding to human foam cells (THP-1 foam) as defined above compared to its binding to human cells prepared by activating THP-1 cells for 24 hours with a mixture of $2\times10^{-7}$M phorbol 12-myristate 13-acetate (PMA) and $0.5\times10^{-7}$M retinoic acid (RA), and afterwards culturing them for 48 hours under lipid-free conditions (THP-1+PMA/RA), and with said monoclonal antibody being further characterized in that it binds an antigen recognized by the monoclonal antibody 3.A9F5E1 as deposited in the ECACC collection under No. 93102638 on Oct. 26, 1993.

ECACC stands for European Collection of Animal Cell Cultures Division of Biologics, Salisbury, Wiltshire SP4 0JG, U.K.

For simplicity, the monoclonal antibody "3.A9F5E1" will be further abbreviated as "3.A9".

As demonstrated in the Examples section, the monoclonal antibody 3.A9 as deposited in the ECACC under No. 93102638 is able to immunoprecipitate an antigen, referred to as the 3.A9 antigen in the examples section. This specific embodiment of the present invention thus encompasses any monoclonal antibody showing an increased binding to THP-1 foam cells versus THP-1+PMA/RA cells and which binds to the 3.A9 antigen.

According to an even more preferred embodiment, the present invention relates to a monoclonal antibody as defined above, further characterized in that it binds to a 150 kDa component such as present on KG-1a cells as determined by means of immunoprecipitation and SDS-PAGE.

KG-1a cells are available from the American Type Culture Collection (ATCC), 12301 Parklawn Drive, Rockville, Md. 20852-1776, U.S.A. (ATCC CCL 246.1, deposited Dec. 12, 1984).

As shown in the Examples section of the present invention, immunoprecipitation and SDS-PAGE analysis of the $^{125}$I-labelled 3.A9 antigen obtained from radiolabelled and lysed KG-1a cells results in a band of apparent molecular weight of 150 kDa when run under reducing conditions on 7.5% gels.

The term "reducing conditions" refers to the addition of 2-mercaptoethanol in the sample buffer.

According to an even more preferred embodiment, the present invention relates to a monoclonal antibody as defined above, further characterized in that it binds to ICAM-3, and not to ICAM-1 or ICAM-2.

As shown in the Examples section of the present invention (especially FIG. 2), the monoclonal antibody 3.A9 as well as 8 previously disclosed anti-ICAM-3 and 3 previously disclosed CDw50 monoclonal antibodies bind to the material eluted from an immunoaffinity column prepared with monoclonal antibody 3.A9. The specificity of this reaction is illustrated by the fact that monoclonal antibodies directed against ICAM-1, ICAM-2, or other molecules showed no binding when applied under similar conditions on the immunopurified material.

According to the most preferred embodiment, the present invention relates to a monoclonal antibody as defined above designated as 3.A9F5E1 and deposited in the ECACC under No. 93102638 on Oct. 26, 1993.

According to yet another embodiment, the present invention relates to a monoclonal antibody as defined above, such as prepared by the process comprising the steps of:

(a) immunizing an animal with KG-1a cells, (b) fusing the spleen cells of said animal with myeloma cells to form antibody secreting hybridoma cells, (c) screening the hybridoma cells for production of monoclonal antibodies directed against KG-1a cells, and, (d) screening the hybridoma cells scoring positive in step (c) for production of a monoclonal antibody which shows an increased binding to THP-1 foam cells as defined above compared to its binding to THP-1+PMA/RA cells as defined above, (e) culturing the selected hybridoma according to step (d) in an appropriate culture medium, (f) recovering the monoclonal antibodies secreted by the selected hybridoma's cultured as in (e), or alternatively, (g) implanting the selected hybridoma's as in (e) into the peritoneum of a mouse and, when ascites has been produced by the animal, recovering the monoclonal antibodies then formed from said ascites.

Monoclonal antibodies are prepared using the method of Kohler and Milstein (1975), or a modification thereof. Typically, a mouse or rat is immunized as described in the examples section. The spleen (and optionally several large lymph nodes) are removed and dissociated into single cells. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the desired immunizing cell-surface antigen (and which do not bind to unrelated antigens). The selected mAb-secreting hybridomas are then cultured either in vitro (e.g., in tissue culture bottles or hollow fiber reactors), or in vivo (as ascites in mice).

Monoclonal antibody 3.A9 was prepared as described in the Examples section herein. Other monoclonal antibodies of the invention may be prepared similarly, or as described above.

According to yet another embodiment, the present invention relates to an antibody derivative, such as an antibody fragment, or a humanized monoclonal antibody, or a single chain antibody, or a labelled monoclonal antibody, with said derivatives being derived from a monoclonal antibody as defined above.

As used herein, the term "humanized antibodies" means that at least a portion of the framework regions of an immunoglobulin are derived from human immunoglobulin sequences.

As used herein, the term "single chain antibodies" refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

If desired, the antibodies (whether polyclonal or monoclonal) may be labelled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase (HRP) is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a mAb. Further, one may combine various labels for desired effect. For example, mAbs and avidin also require labels in the practice of this invention: thus, one might label a mAb with biotin, and detect its presence with avidin labelled with $^{125}I$, or with an anti-biotin mAb labelled with HRP. Other permutations and possibilities will be readily apparent to those of ordinary skill in the art, and are considered as equivalents within the scope of the invention.

According to another embodiment, the present invention also relates to a hybridoma cell line producing a monoclonal antibody as defined above.

According to yet another embodiment the present invention relates to a method for producing a monoclonal antibody as defined above, with said process comprising at least the following steps:

(a) immunizing an animal with KG-1a cells, (b) fusing the spleen cells of said animal with myeloma cells to form antibody secreting hybridoma cells, (c) screening the hybridoma cells for production of monoclonal antibodies directed against KG-1a cells, and, (d) screening the hybridoma cells scoring positive in step (c) for production of a monoclonal antibody which shows an increased binding to THP-1 foam cells as defined above compared to its binding to THP-1+PMA/RA cells as defined above, (e) culturing the selected hybridoma according to step (d) in an appropriate culture medium, (f) recovering the monoclonal antibodies secreted by the selected hybridoma's cultured as in (e), or alternatively, (g) implanting the selected hybridoma's as in (e) into the peritoneum of a mouse and, when ascites has been produced by the animal, recovering the monoclonal antibodies then formed from said ascites.

According to another embodiment, the present invention relates to a method for producing a hybridoma cell line as defined above, comprising the steps (a) to (d) as defined above.

According to another embodiment, the present invention relates to a hybridoma cell line such as prepared according to the method as disclosed above, comprising the steps (a) to (d) as defined above.

According to another embodiment, the present invention relates to a monoclonal antibody as defined above such as prepared by a process comprising the following steps:

(a) culturing a hybridoma cell line according to as defined above in an appropriate culture medium, (b) recovering the monoclonal antibodies secreted by the selected hybridoma's cultured as in (a), or alternatively, (c) implanting the selected hybridoma's as in (a) into the peritoneum of a mouse and, when ascites has been produced by the animal, recovering the monoclonal antibodies then formed from said ascites.

According to another embodiment, the present invention relates to a monoclonal antibody or derivative thereof as defined above for use as a medicament, more particularly monoclonal antibody 3.A9 for curing or suppressing inflammation.

The present invention relates more particularly to monoclonal antibodies as defined above for curing or suppressing inflammation. This aspect of the present invention derives from the ability of ICAM-3 and its functional derivatives to interact with receptors of the leucointegrin family of molecules, especially LFA-1. By virtue of the ability of ICAM-3 to interact with LFA-1, the antibodies against ICAM-3 according to the present invention may be used to suppress (i.e. to prevent, or attenuate) inflammation.

The term "inflammation", as used herein, is meant to include both the reactions of the specific defense system, and the reactions of the non-specific defense system.

According to another preferred embodiment, the present invention relates to monoclonal antibodies as defined above for curing or suppressing specific inflammation, more particularly for curing or suppressing inflammation in response to a condition selected from the group consisting of delayed type hypersensitivity reaction, psoriasis, an autoimmune disease, organ transplant (or tissue graft rejection).

As used, herein, the term "specific defense system" is intended to refer to that component of the immune system that reacts to the presence of specific antigens. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases, and delayed type hypersensitivity response mediated by T-cells (as seen, for example in individuals who test "positive" in the Mantoux test). Chronic inflammatory diseases and the rejection of solid transplanted tissue and organs (e.g. kidney) and non-solid organs such as bone marrow transplants, are further examples of inflammatory reactions of the specific defense system.

As discussed above, the binding of ICAM-3 molecules to LFA-1 is of central importance in cellular adhesion. Through the process of adhesion, lymphocytes are capable of continually monitoring an animal for the presence of foreign antigens. Although these processes are normally desirable, they are also the cause of solid organ transplant rejection (e.g. kidney), non-solid organ transplant rejection (e.g. bone marrow), tissue graft rejection and many autoimmune diseases. Hence, any means capable of attenuating or inhibiting cellular adhesion would be highly desirable in recipients of solid organ transplants (especially kidney transplants), non-solid organ transplants (especially bone marrow transplants), tissue grafts, or for autoimmune patients.

Monoclonal antibodies to members of the leucointegrin family inhibit many adhesion dependent functions of leukocytes including binding to endothelium (Haskard et al., 1986), homotypic adhesions (Rothlein et al., 1986), antigen and mitogen induced proliferation of lymphocytes (Davignon et al., 1981), antibody formation (Fischer et al., (1986), and effector functions of all leukocytes such as lytic activity of cytotoxic T cells (Krensky et al., 1984), macrophages (Strassman et al., 1986), and all cells involved in antibody-dependent cellular cytotoxicity reactions (Kohl et al., 1984). In all of the above functions, the antibodies inhibit the ability of the leukocyte to adhere to the appropriate cellular substrate which in turn inhibits the biological function associated with binding. Such functions, to the extent that they involve ICAM-3/LFA-1 interactions, can be suppressed with anti-ICAM-3 antibodies.

Thus, monoclonal antibodies capable of binding to ICAM-3, such as the monoclonal antibodies according to the present invention, can be employed as an anti-inflammatory agent in a mammalian subject. Significantly, such agents differ from general anti-inflammatory agents in that they are capable of selectively inhibiting adhesion, and do not offer other side effects, such as nephrotoxicity, which are found with conventional agents.

ICAM-3 mediates, in part, adhesion events necessary to mount inflammatory reactions such as delayed type hypersensitivity reactions. Thus, antibodies (especially monoclonal antibodies) capable of binding to ICAM-3 have therapeutic potential in the attenuation or elimination of such reactions.

These potential therapeutic uses may be exploited in either of two manners. First, a composition containing an anti-ICAM-3 monoclonal antibody may be administered to a patient experiencing delayed type hypersensitivity reactions. For example, such compositions might be provided to an individual who had been in contact with antigens such as poison ivy, poison oak, etc. In another embodiment, a monoclonal antibody capable of binding to ICAM-3 is administered to a patient in conjunction with an antigen in order to prevent a subsequent inflammatory reaction. Thus, the additional administration of an antigen with an anti-ICAM-3 antibody can act to temporarily tolerize an individual to subsequent presentation for that antigen.

Since Leukocyte Adherence Deficiency Disease (LAD) patients that lack LFA-1 do not mount an inflammatory response, it is believed that antagonism of LFA-1's natural ligands, will also inhibit an inflammatory response. The ability of antibodies against ICAM-3 to inhibit inflammation provides the basis for their therapeutic use in the treatment of chronic inflammatory diseases and autoimmune diseases such as lupus erythematosus, autoimmune thyroiditis, experimental allergic encephalomyelitis (EAE), multiple sclerosis, some forms of diabetes, Reynaud's syndrome, rheumatoid arthritis, etc. Such antibodies may also be employed as a therapy in the treatment of psoriasis.

In general, the anti-ICAM-3 antibodies of the present invention may be administered alone or in combination with other anti-ICAM-3 and/or anti-ICAM-1 and/or anti-ICAM-2 antibodies in the treatment of those diseases currently treatable through steroid therapy.

In accordance with the present invention, such inflammatory and immune rejection responses may be suppressed (i.e. either prevented or attenuated) by providing to a subject in need of such treatment an amount of an anti-inflammatory agent sufficient to suppress said inflammation. Suitable anti-inflammatory agents include: an antibody capable of binding to ICAM-3; a fragment of said antibody, said fragment being capable of binding to ICAM-3; substantially pure ICAM-3.

The invention further includes the above-described methods for suppressing an inflammatory response of the specific defense system in which an immunosuppressive agent is additionally provided to the subject. Such an agent is preferably provided at a dose lower (i.e. a "sub-optimal" dose) than that at which it would normally be required. The use of a sub-optimal dose is possible because of the synergistic effect of the agents of the present invention. Examples of suitable immunosuppresive agents include but are not limited to dexamethasone, azathioporine, ICAM-1, ICAM-2, or cyclosporin A.

Anti-ICAM-3 antibodies can be used to prevent solid organ or tissue rejection, e.g. kidney, non-solid organ rejection, e.g. bone marrow, or modify autoimmune responses, in the mammalian subject. Importantly, the use of monoclonal antibodies capable of recognizing ICAM-3 may permit one to perform organ transplants even between individuals having HLA mismatch.

According to another embodiment, the present invention relates to a monoclonal antibody as defined above for curing or suppressing non-specific inflammation in response to a condition selected from the group consisting of: adult respiratory distress syndrome (ARDS), multiple organ injury syndromes secondary to septicemia, trauma or hemorrhage, reperfusion injury of myocardial or other tissues, acute glomerulonephritis, reactive arthritis, dermatoses with acute inflammatory components, acute purulent meningitis or other central nervous system inflammatory disorders (e.g. stroke), thermal injury, hemodialysis, leukapheresis, ulcerative colitis, Crohn's disease, necrotizing enterocolitis, granulocyte transfusion associated syndromes, and cytokine-induced toxicity.

As used herein, a reaction of the "non-specific defense system" is intended to refer to a reaction mediated by leukocytes which are incapable of immunological memory. Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia, trauma or hemorrhage, reperfusion injury of myocardial or other tissues; acute glomerulonephritis; reactive arthritis; dermatoses with acute inflammatory components; acute purulent meningitis or other central nervous system inflammatory disorders such as stroke; thermal injury; hemodialysis; leukapheresis; ulcerative colitis; Crohn's disease; necrotizing enterocolitis; granulocyte transfusion associated syndromes; and cytokine-induced toxicity.

According to another embodiment, the present invention relates to a monoclonal antibody as defined above for curing or suppressing the metastasis of a hematopoietic tumor cell, said cell requiring a functional member of the CD11/18 family for migration and said agent is provided to said subject in amount sufficient to suppress said metastasis.

According to yet another embodiment, the present invention relates to a monoclonal antibody as defined above for curing or suppressing the extravascular migration of virally infected leukocytes and said ICAM-3 modulating agent is administered to a subject having such leukocytes in an amount sufficient to suppress the migration of said leukocyte.

According to yet another embodiment, the present invention relates to a monoclonal antibody as defined above for curing or suppressing the migration of cells associated with an asthmatic response and said ICAM-3 modulating agent is provided to said subject in an amount sufficient to suppress the cellular migration associated with asthma.

In this embodiment of the present invention an agent capable of modulating LFA-1/ICAM-3 interactions is used in the treatment of asthma. Specifically, said method comprises administering an effective amount of an anti-asthma agent to an individual in need of such treatment.

The anti-asthma agents of the present invention include the anti-ICAM-3 antibodies as defined above which are capable of impairing the ability of a cell to bind to LFA-1. Antibodies which bind to ICAM-3 will suppress the migration of eosinophils by impairing the ability of the ICAM-3 expressed on these cells to bind to cells expressing a LFA-1 receptor.

The anti-asthma agents of the present invention are intended to be provided to recipient subjects in an amount sufficient to lessen or attenuate the severity, extent or duration of the asthma symptoms.

The agents of the present invention may be administered either alone or in combination with one or more additional anti-asthma agents (such as methylxanthines (such as theophylline), beta-adrenergic agonists (such as catecholamines, resorcinols, saligenins, and ephedrine-, glucocorticoids (such as hydrocortisone)), in order to decrease the amount of such agents needed to treat the asthma symptoms.

The administration of the agents of the present invention may be for either a "prophylactic" or "therapeutic" purpose. When provided prophylactically, the agent is provided in advance of any asthma symptom. The prophylactic administration of the agent serves to prevent or attenuate any subsequent asthmatic response. When provided therapeutically, the agent is provided at (or shortly after) the onset of a symptom of asthma.

The therapeutic administration of the agent serves to attenuate any actual asthmatic episode. The agents of the present invention may, thus, be provided either prior to the onset of an anticipated asthmatic episode (so as to attenuate the anticipated severity, duration or extent of the episode) or after the initiation of the episode.

According to another embodiment, the present invention relates to a peptide of about 5 to about 100 amino acids long which specifically forms an immunological complex with any of the monoclonal antibodies as defined above, with said peptide being possibly in the glycosylated form.

Peptides according to the present invention may be prepared by solid phase according to the methods described by Atherton and Shepard in their book titled "Solid phase peptide synthesis" (IRL Press, Oxford, 1989). Glycosylated peptides may be synthetically prepared according to Peters et al; 1991, or any other technique known in the art. Said peptides according to the present invention may also be prepared by means of recombinant DNA technology.

In this particular embodiment of the present invention, a peptide, more particularly the specific binding epitope of any of the monoclonal antibodies of the present invention is encompassed. In a preferential embodiment, the particular epitope of the monoclonal antibody 3.A9 present on ICAM-3 is encompassed. It should be stressed in this respect that it may not be excluded that the monoclonal antibody 3.A9 binds to a special form or subclass of ICAM-3 which is as to yet not identified further. Peptides according to this embodiment of the invention may be from 5 to about 100 amino acid long. The peptides may be in the form of labelled peptides according to any of the techniques known in the art. The peptides according to this embodiment of the invention may also be used as medicaments for all possible types of treatment known by the man skilled in the art, more particularly for interfering with the interactions of ICAM-3 with members of the leuco-integrin family. Such interactions are important in diseases such as outlined in details above.

A polypeptide of the invention may also consist of or comprise in its amino acid sequence a peptide as defined above, with said polypeptide being different from ICAM-3, such as disclosed in Fawcett et al, (1992), Vaseux et al, (1992), de Fougerolles et al, (1993), WO 92/22323 and WO 93/14776.

The peptides of the invention may be labelled according to any of the techniques known in the art. The polypeptides according to this embodiment of the invention may also be used as medicaments for all possible types of treatment known by the man skilled in the art. For instance, they may be used to suppress inflammation.

According to another embodiment, the present invention relates to a pharmaceutical composition containing, as active substance, a monoclonal antibody or a derivative thereof or a peptide, or polypeptide as defined above.

According to another embodiment, the present invention relates to the use of a monoclonal antibody or a derivative thereof or a peptide, as defined above for the preparation of a medicament for treating any of the diseases selected from the group of:

specific inflammation in response to a condition selected from the group consisting of delayed type hypersensitivity reaction, a symptom of psoriasis, an autoimmune disease, organ transplant (or tissue graft rejection);

non-specific inflammation in response to a condition selected from the group consisting of:

adult respiratory distress syndrome (ARDS), multiple organ injury syndromes secondary to septicemia, trauma or hemorrhage, reperfusion injury of myocardial or other tissues, acute glomerulonephritis, reactive arthritis, dermatoses with acute inflammatory components, acute purulent meningitis or other central nervous system inflammatory disorders (e.g. stroke), thermal injury, hemodialysis, leukapheresis, ulcerative colitis, Crohn's disease, necrotizing enterocolitis, granulocyte transfusion associated syndromes, and cytokine-induced toxicity, metastasis of a hematopoietic tumor cells, extravascular migration of virally infected leukocytes, asthma, etc.

The antibodies of this invention are administered at a concentration that is therapeutically effective to prevent or treat any of the afore-mentioned disease states. To accomplish this goal, the antibodies may be formulated using a variety of acceptable excipients known in the art. Typically, the antibodies are administered by injection, either intravenously or intraperitoneally. Methods to accomplish this administration are known to those of ordinary skill in the art. It may also be possible to obtain compositions which may be topically or orally administered, or which may be capable of transmission across mucous membranes.

Before administration to patients, formulants may be added to the antibodies. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a C4 to C8 hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP patent applications No. EP 0 270 799 and EP 0 268 110.

Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337: 4,495,285; and 4,609,546. Preferred polymers are polyoxyethylated polyols and polyethylene glycol (PEG). PEG is soluble in water at room temperature and has the general formula: R(O—CH2—CH2)nO—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated. However, it will be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, and a discussion of POG/IL-2 conjugates is found in U.S. Pat. No. 4,766,106.

Another drug delivery system for increasing circulatory half-life is the liposome. Methods of preparing liposome delivery systems are discussed in Gabizon et al., 1982; and Szoka, 1980. Other drug delivery systems are known in the art and are described in, e.g. Poznansky, 1984.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, the antibodies and compositions of this invention are used to treat human patients to prevent or treat any of the above-defined disease states. The preferred route of administration is parenterally. In parenteral administration, the compositions of this invention will be formulated in a unit dosage injectable form such as a solution, suspension or emulsion, in association with a pharmaceutically acceptable parenteral vehicle. Such vehicles are inherently nontoxic and nontherapeutic. Examples of such vehicles are saline, Ringer's solution, dextrose solution, and Hanks' solution. Nonaqueous vehicles such as fixed oils and ethyl oleate may also be used. A preferred vehicle is 5% dextrose in saline. The vehicle may contain minor amounts of additives such as substances that enhance isotonicity and chemical stability, including buffers and preservatives.

The dosage and mode of administration will depend on the individual. Generally, the compositions are administered so that antibodies are given at a dose between 1 μg/kg and 20 mg/kg, more preferably between 20 μg/kg and 10 mg/kg, most preferably between 1 and 7 mg/kg. Preferably, it is given as a bolus dose, to increase circulating levels by 10–20 fold and for 4–6 hours after the bolus dose. Continuous infusion may also be used after the bolus dose. If so, the antibodies may be infused at a dose between 5 and 20 μg/kg/minute, more preferably between 7 and 15 μg/kg/minute.

According to an equally preferred embodiment, the present invention relates to the use of a monoclonal antibody or a derivative thereof or a peptide, for the preparation of diagnostic or in vivo imaging means of any of the above-mentioned disease states.

Since ICAM-3 is expressed mostly at sites of inflammation, a chimeric antibody capable of binding ICAM-3 may be employed as a means of imaging or visualizing the sites of infection and inflammation in a patient.

According to a preferred embodiment an antibody, fragments, analogs, and derivatives thereof are detectably labelled through the use of halogen radioisotopes such as $^{131}$I, $^{125}$I, metallic radionuclides $^{67}$Cu, $^{111}$In, $^{67}$Ga, $^{99}$Tc, etc.; affinity labels (such as biotin, avidin, etc.) fluorescent labels, paramagnetic atoms, etc and is provided to a patient to localize the site of infection or inflammation. Procedures for accomplishing such labeling are well known to those skilled in the art. Clinical application of antibodies in diagnostic imaging are reviewed by Grossman, 1986; Unger et al., 1985, Khaw et al., 1980.

The detection of foci of such detectably labelled antibodies is indicative of a site of inflammation, tumor development or atherosclerotic plaques. In one embodiment, this examination for inflammation is done by removing samples of tissue, including blood cells, and incubating such samples in the presence of the detectably labeled antibodies. In a preferred embodiment, this technique is done in a non-invasive manner through the use of magnetic resonance imaging (MRI), single photon emission computed tomography (SPECT) or fluorography and extracorporal detecting means (Perkins et al., 1988, Mach et al., 1991), etc. Such a diagnostic test may be employed in monitoring organ transplant recipients for early signs of potential tissue rejection. Such assays may also be conducted in efforts to determine an individual's predilection to rheumatoid arthritis or other chronic inflammatory diseases.

According to another embodiment the present invention relates to the use of a monoclonal antibody or a derivative thereof, as defined above for the preparation of diagnostic and in vivo imaging means of atherosclerosis.

The present invention will now be illustrated by reference to the following examples which set forth particularly advantageous embodiments. However, it should be noted that these embodiments are illustrative and are not to be construed as restricting the invention in any way.

List of Abbreviations

AP: alkaline phosphatase
BSA: bovine serum albumin
CD: cluster of differentiation
CHAPS: 3-[(3-cholamidopropyl)-dimethylammonio]-1-propanesulfonate
D'PBS: Dulbecco's phosphate buffered saline without $Ca^{2+}$ and $Mg^{2+}$
EDTA: ethylenediaminetetraacetic acid disodium salt
FACS: fluorescence activated cell sorter
FCS: foetal calf serum
FITC: fluorescein isothiocyanate
HPLC: high performance liquid chromatography
ICAM: intercellular adhesion molecule
LDL: low density lipoprotein
LFA-1: lymphocyte function-associated antigen-1
LPDS: lipoprotein-deficient serum
mAb: monoclonal antibody
MFI: mean fluorescence intensity
NP-40: Nonidet P-40
NRS: normal rabbit serum
PAGE: polyacrylamide gel electrophoresis
PBS: phosphate buffered saline
PEG: polyethylene glycol
PMA: phorbol 12-myristate 13-acetate
PMSF: phenylmethylsulfonyl fluoride
RA: retinoic acid
SDS: sodium dodecyl sulfate
THP-1+PMA/RA: THP-1 cells activated with a mixture of $2\times10^{-7}$M PMA and $0.5\times10^{-7}$ M RA for 24 hours and then cultured for 48 hours under lipid-free conditions
THP-1 foam: THP-1 cells activated with a mixture of $2\times10^{-7}$ M PMA and $0.5\times10^{-7}$ M RA for 24 hours and subsequently incubated for 48 hours with aggregated low density lipoproteins
VLA: very late activation antigen

BRIEF DESCRIPTION OF FIGURES

FIG. 1A: $^{125}$I-labelled KG-1a cell extract was immunoprecipitated with mAb 3.A9 and analyzed by 7.5% SDS-PAGE under reducing (lane 1) or non-reducing (lane 2) conditions. Molecular weight markers (200 kDa, 97 kDa, 69 kDa are shown on the left). FIG. 1B: $^{125}$I-labelled KG-1a cell extract was precipitated with mAb 1.24 (isotype control) (lane 2), TS2/9 (CD58) (lane 3), 3.A9 (lane 4), CLB-LFA-1/2 (CD11a) (lane 5), CLB-LFA-1/1 (CD18) (lane 6) and HP2/1 (anti-VLA-4) (lane 7). Molecular weight markers (200 kDa, 97 kDa, 69 kDa, 46 kDa respectively) are shown in lane 1.

FIG. 2: Binding of 3.A9, anti-ICAM-3, CDw50 and control antibodies on affinity-purified 3.A9 antigen. 3.A9 antigen was purified by affinity chromatography from human spleen cell extract. Eluate fractions were coated on microtiter plates and tested for binding to 3.A9, anti-ICAM-3, CDw50 and control antibodies by enzyme-linked immunoassay.

FIG. 3: Up-regulation of 3.A9 antigen on THP-1 foam cells. mAb 3.A9 was tested by indirect immunofluorescence on THP-1 cells in three differentiation stages (THP-1, THP-1+PMA/RA, THP-1 foam; for a definition of these cell populations see example 6). mAb 3.A9 shows an enhanced binding on THP-1 foam cells in comparison with THP-1 and THP-1+PMA/RA cells in all nine experiments performed. Mean fluorescence intensity (on a four decade log scale) (MFI) is given.

FIG. 4: Behaviour of 3.A9, CDw50 and anti-ICAM-3 mAb in our foam cell model. mAb 3.A9 together with the other anti-ICAM-3 and CDw50 mAb at our disposal were tested by flow cytometry on THP-1 cells in three differentiation stages (THP-1, THP-1+PMA/RA and THP-1 foam; for a definition of these cell populations see example 6). mAb 3.A9 is the only anti-ICAM-3 or CDw50 mAb that shows enhanced binding on THP-1 foam cells in comparison with THP-1 and THP-1+PMA/RA cells. Mean fluorescence intensity (on a four decade log scale) (MFI) is given.

FIGS. 7A and 7B: Up-regulation of the CD36 molecule on THP-1 foam cells. FIG. 7A: mAb OKM5 was tested by flow cytometry on THP-1, THP-1+PMA/RA and THP-1 foam cells. OKM5 shows an enhanced binding on THP-1 foam cells in comparison with THP-1 and THP-1+PMA/RA cells. FIG. 7B: FACS histogram of OKM5 mAb on three populations of THP-1 cells.

EXAMPLES

Example 1

Figure 1A:
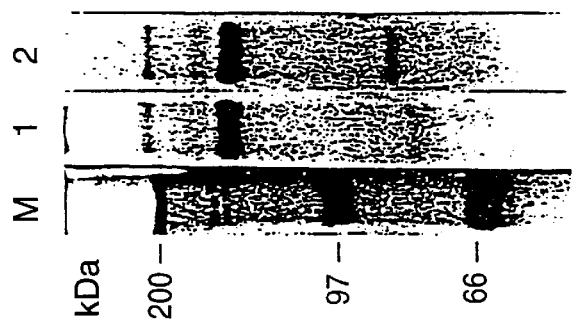
FIGS. 1A and 1B: Immunoprecipitation of 3.A9 antigen.

Generation of a New Human THP-1 In Vitro Foam Cell Model

LDL Preparation and Modification

Human LDL (d=1.019–1.063 kg/l) were isolated from fresh plasma by sequential flotation ultracentrifugation and lipoprotein-deficient serum (LPDS) was obtained as previously described (Vercaemst et al., 1989). These preparations were dialyzed extensively against 0.15 M NaCl, 0.01% ethylenediaminetetraacetic acid disodium salt (EDTA), pH 7.4, filtered through a 0.22 μm MILLEX™ GV filter (Millipore, Bedford, Mass.) and stored at 4° C.

Acetylated LDL was prepared as described (Vercaemst et al., 1989). Aggregated LDL particles were obtained by sonication of native LDL (5–10 mg/ml) under sterile conditions during 10×15 seconds with 15 seconds time intervals, using a Branson microtip probe (Danbury, Conn.) at 52° C. and an output of 60 Watt. The degree of aggregation was followed by measuring the optical density at 680 nm as described (Khoo et al., 1988). Therefore, samples were diluted to 40 μg/ml in phosphate-buffered saline (PBS). The electrophoretic mobility of the lipoproteins was verified by agarose gel electrophoresis, using pre-cast agarose gels and Universal Barbital buffer, pH 8.6 (Ciba Corning, Palo Alto, Calif.) according to the method of Basu et al. (1979).

The chemical composition of the aggregates remained unchanged compared to native LDL. On agarose gels, a minor fraction was detected with a mobility of LDL, whereas the majority of particles did not enter the gel, due to their high molecular weight. High performance liquid chromatography (HPLC) gelfiltration demonstrated the presence of aggregated LDL with a MW of >7.5×106 dalton (Da). The chromatographic separation of lipoproteins using gelfiltration was performed as described by Vercaemst et al. (1983) with a Spectra-Physics SP 8000 HPLC. Fifty μl lipoprotein sample (+2 mg/ml) was loaded on an Ultro Pac TSK-G 4000 SW column (60 cm×7.5 mm; Pharmacia LKB, Uppsala, Sweden), eluted with 0.2 M Na2HPO4 and a flow of 0.5 ml/minute. Protein was detected at 280 nm. Transmission electron microscopy of aggregated LDL was performed as described by Forte and Nordhausen (1986). Lipoprotein samples were diluted to 150 μg/ml in 125 mM ammonium acetate, 2.6 mM ammonium carbonate, 0.27 mM EDTA, pH 7.4 and dialyzed overnight at 4° C. Equal volumes of lipoprotein sample and 2% phosphotungstic acid, pH 7.4 were mixed, and 10 μl was applied on a Formvar grid (Balzers, Liechtenstein). Preparations were viewed with a Zeiss EM 10C electron microscope and revealed a heterogenous population of particles with a diameter varying between 20 and 100 nm.

Cell Culture and Foam Cell Formation

The THP-1 cell line was obtained from The American Type Culture Collection (ATCC TIB 202; Rockville, Md.). Cells were maintained in RPMI 1640 medium (Gibco Laboratories, Grand Island, N.Y.) containing 10% fetal calf serum (FCS; Gibco) in a humidified incubator with 5% carbon dioxide at 37° C. To induce foam cell formation, THP-1 cells were seeded in 35 mm wells (Nunc, Roskilde, Denmark) at $1\times10^6$ cells/ml in 2 ml RPMI 1640 medium in the presence of 10% FCS, $2\times10^{-7}$ M PMA (Cat No P8139, Sigma, St. Louis, Mo.), $0.5\times10^{-7}$ M all-trans retinoic acid (RA) (Cat No R2625, Sigma) and incubated for 24 hours. Subsequently, cells were washed two times by aspiration with 2 ml RPMI 1640 without FCS, and incubated for 48 hours in 2 ml RPMI 1640 containing 10% LPDS, 25 μg/ml gentamycin (Gibco), with or without 200 μg/ml of aggregated LDL. Taken together, three populations of THP-1 cells were under investigation: (a) cells grown in RPMI 1640 in the presence of 10% FCS (THP-1), (b) PMA/RA differentiated cells that were further grown for 48 hours under lipid-free conditions (THP-1+PMA/RA), and (c) PMA/RA differentiated cells that were further grown for 48 hours in the presence of aggregated LDL in order to induce foam cell formation (THP-1 foam).

Cellular free cholesterol and cholesteryl esters were determined by reversed-phase HPLC as described (Vercaemst et al., 1989). At the end of the cholesterol-loading incubation period, the medium was removed from the dishes and the adherent cells were washed once with PBS, 0.2% bovine serum albumin (BSA), twice with PBS alone and scraped into PBS with a rubber policeman. About $2\times10^6$ cells were extracted with 5 ml hexane/isopropanol (3:2, v/v; Merck, Darmstadt, FRG) containing 50 μl of cholesteryl heptadecanoate (1.2 mg/ml chloroform; Sigma) as an internal standard. After centrifugation at 1800 g for 15 minutes, the organic phase supernatant was dried under nitrogen and the precipitate was dissolved in 1 ml chloroform and washed three times. The dry residue was finally dissolved in 10 μl chloroform and 40 μl of elution solvent, being acetonitrile/isopropanol (1:1, v/v). Twenty μl was injected for HPLC analysis (Vercaemst et al., 1989). The protein pellet was dissolved in 0.1 M NaOH and the protein content was determined by the BCA Protein Assay Reagent kit (Pierce, Rockford, Ill.), using BSA as a standard. Cholesterol masses were expressed as μg per mg cell protein.

THP-1 foam cells accumulated an average intracellular cholesterol amount of 139+36 μg/mg cell protein, of which 46+6% was obtained in the esterified form. Foam cell formation was only induced by addition of aggregated LDL to PMA/RA differentiated THP-1 cells. Prior induction with PMA alone did not result in similar high cholesterol contents (Table 1). Addition of native or acetylated LDL to PMA/RA differentiated THP-1 cells only resulted in a slight increase in lipoprotein uptake, comparable to PMA differentiation alone. The erythroleukemic K-562 cell line (ATCC CCL 243) that was used in an analogous experimental design could not be induced to accumulate equal cholesterol amounts as found in THP-1 foam cells (Table 1). Addition of aggregated LDL upon PMA/RA differentiation resulted in only 30 μg total cholesterol per mg cell protein, and a low degree of esterification was observed.

For Oil Red O staining of cellular lipids, THP-1 cells were grown on Lab Tek slides (Nunc), washed with PBS and fixed in formol vapour for 15 minutes. Cytospins of suspension cells were fixed in 4% formaldehyde solution for 7 minutes. Preparations were immersed during 2 minutes in propylene glycol, rinsed with distilled water in a petridish and stained with a filtered solution of 5 mg/ml Oil Red O (Aldrich, Milwaukee, Wis.) in propylene glycol for 1 hour. They were rinsed in 85% propylene glycol (1 minute), and washed in distilled water. PMA/RA differentiated THP-1 cells showed a lot of extrusions and few cytoplasmic Oil Red O stainable droplets were visible. Upon addition of aggregated LDL, numerous stained droplets were detected, proving the intracellular uptake of the particles. For electron microscopy, cells were grown on glass cover slips in 35 mm well plates, washed twice with cold PBS and fixed with 2.5% glutardialdehyde in 0.1 M cacodylate, pH 7.4. Preparations were stained with 1% OsO4 in cacodylate buffer, post-stained with uranyl acetate and lead citrate and examined with a Zeiss EM 10C electron microscope. Suspension THP-1 cells were fixed at a concentration of $10^6$ cells/ml using 2.5% glutardialdehyde during 2 hours. Cytospins were made and processed as mentioned above. Electron microscopy of these foam cells revealed that the majority of the lipid inclusions consisted of cytoplasmic free droplets, beside which also lysosomal lipid structures and large vacuoles filled with debris were detected.

The described in vitro human foam cell model, generated by the addition of aggregated LDL particles for 48 hours to PMA/RA differentiated THP-1 cells, proves to be a better system than the ones described in literature (Hara et al., 1987; Yamamoto et al., 1988), because of the higher amounts of intracellular cholesterol and cholesteryl esters, resembling the in vivo situation.

Example 2

Production of Monoclonal Antibody 3.A9

Immunisation Protocol

Female BALB/c mice were injected intraperitoneally at day 0, 14 and 28 with 2×107 human KG-1a cells (American Type Culture Collection CCL 246.1) in 200 μl of Dulbecco's PBS without $Ca^{2+}$ and $Mg^{2+}$ (D'PBS).

Fusion, Selection and Cloning Protocol

Three days after the last immunisation, the spleen of an immune mouse was removed sterilely and a single cell suspension prepared by gentle teasing with forceps. The spleen cells were washed twice for 10 minutes at 200 g in serum-free RPMI 1640 medium. SP2/0-Ag14 mouse myeloma cells (ATCC CRL 1581), kept in log phase in RPMI 1640 with 10% FCS for three days prior to fusion, were centrifuged at 200 g for 10 minutes and likewise washed twice in serum-free RPMI. Mouse spleen cells and SP2/0-Ag14 myeloma cells were fused at a ratio of 10:1 using 50% polyethylene glycol 4000 (Merck). To this end, both cell suspensions (in serum free RPMI) were mixed, centrifuged and the supernatant aspirated. The cell pellet was dislodged by tapping the tube and 2 ml of polyethylene glycol (50% in RPMI, pH 7.4) was added at 37° C. with stirring over the course of 1 minute, followed by adding gently 5 ml of warm (37° C.) serum-free RPMI over 90 seconds. An additional 20 ml warm RPMI was added and the cells were centrifuged at 200 g for 10 minutes. The cell pellet was resuspended in HAT selective medium (RPMI 1640 supplemented with 10% FCS, 2 mM L-glutamine, 1 mM sodium pyruvate, 100 IU/ml penicillin, 100 μg/ml streptomycin, and containing 100 μM hypoxanthine, 0.4 μM aminopterin and 16 μM thymidine, all reagents from Gibco). Cells were cultured in 96-well plastic plates at 37° C. with 5% $CO_2$ in a humid atmosphere. From day 5 onwards, cloning plates were observed carefully with a phase-contrast microscope. Hybrid colonies were visible in 5–14 days and supernatants from these were screened for (a) production of mAb to human KG-1a cells using indirect immunofluorescence (67 wells scored positive on a total of 10 plates=960 wells tested) and (b) for differential binding on THP-1+ PMA/RA and THP-1 foam cells using indirect immunofluorescence (1 scored positive out of 67, namely 3.A9). For details on the staining method, see example 3. Cells from the 3.A9 well were cloned twice by limiting dilution in the presence of mouse spleen cells as feeder layers. Hybridoma 3.A9F5E1 (obtained after two rounds of limiting dilution) was deposited in the "European Collection of Animal Cell Cultures" on Oct. 26th 1993 under accession number 93102638. For simplicity, this hybridoma (3.A9F5E1) and the mAb it secretes are further referred to as 3.A9 in the examples, description and claims. Antibody in the form of ascitic fluid was prepared by injecting 1×106 hybridoma cells intraperitoneally in BALB/c mice treated with pristane (2,6,10,14-Tetramethylpentadecane) (Aldrich). mAb 3.A9 is of the IgG1 kappa subclass as determined with a mAb isotyping kit, making use of strips coated with rat anti-mouse isotype-specific antibodies (Innogenetics, Antwerp, Belgium).

Example 3

Cell Distribution Pattern of Monoclonal Antibody 3.A9

A number of B, T, myeloid and erythroid cell lines and normal blood cells were tested by flow cytometry for their reactivity with mAb 3.A9.

Cells and Cell Lines

The human cell lines (see Table 2) were cultured in RPMI 1640 medium supplemented with 10% FCS, 2 mM L-glutamine, 100 IU/ml penicillin, and 100 μg/ml streptomycin. Peripheral blood mononuclear cells were isolated from anti-coagulated venous blood of healthy volunteers by density gradient centrifugation over cell separation tube prefilled with LYMPHOPREP™ (Nycomed, Oslo, Norway). For this purpose, fresh peripheral blood was mixed with an equal volume of D'PBS, carefully layered upon LYMPHOPREP™ using a Pasteur pipette (8 ml of diluted blood/6 ml of LYMPHOPREP™ in a 15 ml tube) and centrifuged at 400 g for 30 minutes at room temperature. Mononuclear cells were removed from the interface (between the sample layer and the LYMPHOPREP™ solution) using a Pasteur pipette, washed once with D'PBS and once with D'PBS/2% FCS. Neutrophils were collected from the pellet after dextran T500 (Pharmacia) sedimentation and hypotonic lysis of contaminating red blood cells: (a) the pellet (obtained after LYMPHOPREP centrifugation of 10 ml diluted blood, and containing granulocytes and erythrocytes) was resuspended in 10 ml of D'PBS and mixed with dextran (3% w/v in D'PBS) in a ratio of 10 ml cell suspension for 15 ml dextran; (b) erythrocytes were allowed to sediment for 1 hour at room temperature; (c) the supernatant was centrifuged (10 minutes, 250 g) and washed once with D'PBS; (d) contaminating red blood cells were removed by hypotonic lysis; and (e) resulting granulocytes were washed twice with D'PBS and once with D'PBS/2% FCS. Erythrocytes were prepared by removing the buffy coat after centrifugation (15 minutes, 200 g) of whole blood and washing (10 minutes, 600 g) twice with D'PBS and once with D'PBS/2% FCS. Platelets were obtained as follows: (a) centrifugation (15 minutes, 200 g) of whole blood; (b) centrifugation of supernatant (=platelet-rich plasma) for 5 minutes at 1600 g; and (c) washing (5 minutes, 1600 g) of the pellet (=platelets) three times with D'PBS/1% BSA/ 0.05% EDTA.

Flow Cytometry Analysis

Presence or absence of the 3.A9 antigen on these cell types was studied by indirect immunofluorescence as follows. Aliquots of $5\times10^5$–$1\times10^6$ cells (in 100 µl D'PBS/2% FCS/0.02% NaN3) were incubated with a saturating amount (1/250 final dilution of ascitic fluid) of mAb 3.A9 for 30 minutes at 4° C., washed once with D'PBS/2% FCS/0.02% NaN3, incubated for another 30 minutes with fluorescein-isothiocyanate (FITC)-labelled affinity-purified goat F(ab')2 anti-mouse Ig (Tago, Burlingame, Cailf.) and again washed with D'PBS/2% FCS/0.02% NaN3. For platelets, the whole procedure was performed in D'PBS/1% BSA/0.05% EDTA/ 0.02% NaN3 instead of D'PBS/2% FCS/0.02% NaN3. The stained cells (except erythrocytes which were analyzed immediately) were then fixed with 0.5% paraformaldehyde in D'PBS and analyzed using CONSORT 30 software on a FACScan (Becton-Dickinson, Erembodegem, Belgium). Fluorescence was measured with logarithmic amplification on a total of 5000 cells. Where applicable, lymphocytes and monocytes were identified based on 2-dimensional light scatter characteristics. In some experiments, the identity of these cell types was confirmed by staining with mAb specific for monocytes, T cells and B cells (Becton-Dickinson). Heat-inactivated normal rabbit serum (NRS) was added in both the first and second incubation step to avoid aspecific Fc gamma receptor staining.

Results

The results are summarised in Table 2. From Table 2, it is evident that the 3.A9 antigen is a non-lineage antigen present in moderate to large amounts on a lot of cell types tested. Only erythrocytes, platelets, K-562, Daudi and Raji cells do not react with mAb 3.A9. Comparison of its distribution pattern with the "Leucocyte Typing Data Base IV" (Gilks, 1990) reveals that mAb 3.A9 resembles mAb 101-1D2 and 140-11, which during "The Fourth International Workshop and Conference on Human Leucocyte Differentiation Antigens" were clustered in CDw50 (Hadam et al., 1990). As mentioned earlier, it has recently been published that CDw50 antigen and ICAM-3 are one and the same molecule (Juan et al., 1993).

Example 4

Biochemical Characterization of the 3.A9 Antigen
Radiolabelling of Cell Surface Proteins, Immunoprecipitation, Gel Electrophoresis and Autoradiography KG-1a cells were labelled at the surface by lactoperoxidase-catalyzed iodination. For this purpose, $5\times10^7$ cells (in 150 µl D'PBS), 50 µl lactoperoxidase solution (100 IU/ml) (Calbiochem, La Jolla, Calif.), 10 µl 0.5 M phosphate buffer pH 7.0, 1.0 mCi $Na^{125}I$ (Amersham, Buckinghamshire, U.K.) and 20 µl 0.03% $H_2O_2$ were incubated together for 4 minutes at 30° C. An additional 20 µl 0.03% $H_2O_2$ was added and the incubation continued for another 10 minutes at room temperature. The cells were then washed 5 times in D'PBS containing 5 mM potassium iodide and 0.02% NaN3. Radioiodinated cells were lysed in 1.0 ml lysis buffer (50 mM Tris-HCl pH 8.0, containing 150 mM NaCl, 0.5% of the non-ionic, polyoxyethylene octyl detergent NONIDET™ P-40 (NP-40), 100 mM iodoacetamide, 3 mM EDTA, 1 µM pepstatin A, 0.03 trypsin inhibiting units (TIU)/ml aprotinin, 2 mM phenylmethylsulfonyl fluoride (PMSF) and 0.1% NaN3). After 15 minutes at 4° C., the extract was centrifuged at 30,000 g for 1 hour. The resulting supernatant was collected and preadsorbed with protein A-SEPHAROSE™ CL-4B (Pharmacia) for 2 hours at 4° C. For immunoprecipitation, 50 µl ($2$–$3\times10^6$ cell equivalents) of iodinated lysate were mixed with 10–50 µl of appropriately diluted mAb 3.A9 and incubated overnight at 4° C. The antigen-antibody complexes formed were precipitated with 150 µl of 10% protein A-Sepharose (prewashed in lysis buffer and resuspended to a 10% solution in lysis buffer containing 0.1% BSA) for 3 hours at 4° C., washed three times in lysis buffer containing 0.5% deoxycholate and 0.1% BSA, disrupted in sample buffer (containing 15% glycerol, 3% sodium dodecyl sulfate (SDS), 0.01% bromphenol blue in 62 mM Tris buffer pH 6.8 with or without 5% 2-mercaptoethanol) (4 minutes, 95° C.) and analyzed by one-dimensional SDS-polyacrylamide gel electrophoresis (SDS-PAGE) according to Laemmli (1970). After Coomassie staining and drying, the gels were subjected to autoradiography at –80° C. with X-ray film and intensifying screens.

Results

Figure 1B:

Immunoprecipitation and SDS-PAGE analysis of the $^{125}I$-labelled 3.A9 antigen on KG-1a cells results in a band of apparent molecular weight 150 kDa when 7.5% gels were run under reducing conditions (FIG. 1A). A slightly smaller apparent molecular weight was observed under non-reducing conditions (FIG. 1A). In some experiments, weak bands of >200 kDa and of 80 kDa were also observed. In another immunoprecipitation experiment, mAb 3.A9 was compared with mAb TS2/9 (CD58) (a gift of Dr. T. Springer, Boston, Mass.) (Sanchez et al.-Madrid, 1982), CLB-LFA-1/2 (CD11a) (Janssen Biochimica, Beerse, Belgium), CLB-LFA-1/1 (CD18) (Janssen) and HP2/1 (anti-VLA-4) (a gift of Dr. F. Sanchez-Madrid, Madrid, Spain). As is evident from FIG. 1B, the 3.A9 antigen does not correspond to any of these known CD antigens. These data can best be explained by assuming that the 3.A9 antigen has a molecular weight of 150 kDa (the 80 kDa band being a degradation product). Alternatively, the 3.A9 antigen could be an alfal-betal heterodimer where the 150 kDa component is non-covalently associated with the 80 kDa component. There is now a consensus that the CDw50/ICAM-3 antigen has a molecular weight of 116–140 kDa depending on the cell type tested (WO 93/14776; Juan et al., 1993). However, it should be stressed that CDw50 mAb were originally described as precipitating two bands of 110 and 140 kDa (Hadam et al., 1990).

Example 5

Purification of 3.A9 Antigen
Preparation of 3.A9 Affinity Column mAb 3.A9 was purified by Protein G-SEPHAROSE™ affinity chromatography (Pharmacia). Ascitic fluid (diluted 1/2 with PBS pH 7.2) was applied to a Protein G-SEPHAROSE™ column (bed volume 6 ml) and allowed to interact for 30 minutes at room temperature. The column was washed with PBS until no protein could be detected in the wash solution. Bound antibody was eluted with 0.1 M glycin-HCl pH 3.0 and neutralized with a sufficient amount of 10× concentrated PBS. Purified mAb 3.A9 was extensively dialysed against 0.1 M borate buffer pH 8.5 and coupled to the coupling support REACTI-GEL® (Pierce) according to the instructions of the manufacturer. Essentially: (a) excess acetone was removed from the Reacti-Gel support using gentle suction through a Buchner funnel with Whatman paper; (b) the gel was washed quickly several times with ice-cold 0.1 M borate buffer pH 8.5; (c) the gel was mixed immediately with borate buffer containing mAb in the following ratio (1 ml gel/4 ml 0.1 M borate buffer pH 8.5/4 mg mAb 3.A9); (d) the mixture was rotated for 48 hours at 4° C.; (e) after washing with D'PBS the gel was incubated with 1.5 M Tris-HCl pH 8.8 to block remaining active sites; (f) after washing the gel was stored in D'PBS/ 0.02% NaN3 at 4° C.

Preparation of Extract Containing 3.A9 Antigen

Frozen human spleen (80 gram) was cut into small pieces, washed in 0.25 M sucrose/ 10 mM Tris-HCl pH 7.4, and homogenized at 4° C. in a Virtis mixer (3×10 seconds for separate 30 ml fractions) in 200 ml of the same buffer. After centrifugation at 400 g for 10 minutes, the supernatant was ultracentrifuged at 100,000 g for 1 hour at 4° C. The resulting pellet was lysed with 75 ml of ice-cold lysis buffer (composition of the lysis buffer as described in example 4, except that iodoacetamide was omitted) (1 hour at 4° C. with gentle stirring). After ultracentrifugation at 100,000 g for 1 hour, the supernatant was collected. The 100,000 g pellet was subjected to the same procedure and both supernatants combined.

Preparation of Enriched Affinity-Purified 3.A9 Antigen

The extract was passed several times at a rate of 6–24 ml/hour over a precolumn containing 5 ml of the coupling support REACTI-GEL® to which an IgG1 control mAb was bound, followed by a column containing 18 mg of mAb 3.A9 coupled at a ratio of 6 mg/ml to the same the coupling support REACTI-GEL® support. After application of the extract, the column was washed with 10–20 column volumes of: (a) 50 mM Tris-HCl pH 8.0, 0.5 M NaCl, 0.2% NP40, 5 mM EDTA, 1 mM PMSF; and (b) 10 mM Tris-HCl pH 7.4, 0.2% 3-[(3-cholamidopropyl)-dimethylammonio]-1-propanesulfonate (CHAPS), 1 mM PMSF. Antigen was eluted with 5 column volumes of 50 mM diethylamine-HCl pH 11.5 in the presence of 0.2% CHAPS. Fractions of 1 ml were collected from the diethylamine elution in tubes containing sufficient amounts of 1 M glycin-HCl pH 3.0 to neutralize the fraction. Aliquots of each fraction were analyzed by solid-phase indirect antibody binding assay, as described in the following paragraph.

ELISA for Detection of 3.A9 Antigen in Eluate Fractions

Sixty μl of each eluate fraction (1/60 diluted in 50 mM $Na_2CO_3$/$NaHCO_3$ buffer pH 9.6) was incubated overnight at room temperature in microtiter plates (Nunc). The plates were then: (a) washed three times with D'PBS and saturated for 2 hours with D'PBS/1% BSA/1% NRS; (b) incubated with mAb (3.A9, CDw50, anti-ICAM-3, controls, see below) (1/250 dilution in D'PBS/1% BSA) for 2 hours with gentle rocking; (c) washed three times with D'PBS/0.05% Tween-20; (d) incubated with alkaline phosphatase (AP)-labelled rabbit anti-mouse Ig (Dako, Ghent, Belgium) (1/1000 in D'PBS/1% BSA/1% NRS) for 1 hour; (e) washed two times with D'PBS/0.05% Tween-20; (f) washed once with AP-buffer (1 M diethanolamine pH 9.8, 0.5 mM $MgCl_2$); and (g) incubated with substrate (2 mg/ml para-nitrofenylphosphate in AP-buffer). The O.D. at 405 nm was measured after 30 minutes with a plate reader.

Besides 3.A9, the following anti-ICAM-3 and CDw50 mAb were used: CBR-IC3/1 (de Fougerolles and Springer, 1992), CBR-IC3/2 (de Fougerolles et al., 1993), CBR-IC3/3, CBR-IC3/4, CBR-IC3/5, CBR-IC3/6 (mAb CBR-IC3/1, 2, 3, 4, 5, 6 have been described in WO 92/22323), HP2/19 (Carrera et al., 1988), KS 128 (Fawcett et al., 1992), 152-2D11 (Juan et al., 1993), 140-11 (Vilella et al., 1990), 101-1D2 (Vilella et al., 1990). In addition, the following mAb were used as controls: 1.24 (De Smet et al., 1983), 1.C1 (CD43) (De Smet et al., 1993) and 2.E11 (anti-HLA class I) (De Smet et al., 1993).

Results

Figure 5A:
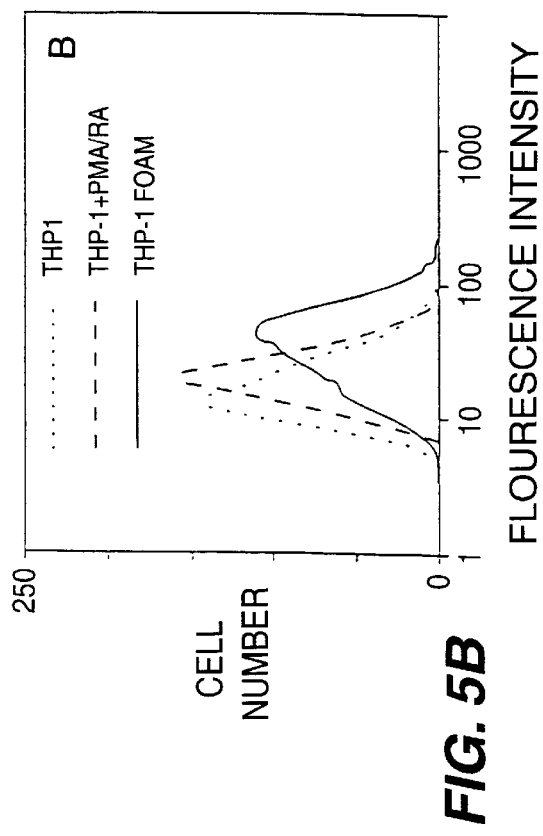
FIGS. 5A, 5B, 5C: Up-regulation of mAb 3.A9, but not of the other CDw50 or anti-ICAM-3 mAb on THP-1 foam cells. FACS histograms of mAb 1.24 (isotype control mAb) (5A), mAb CBR-IC3/1 (representative for the other anti-ICAM-3 and CDw50 mAb) (5B), and mAb 3.A9 (5C) on THP-1, THP-1+PMA/RA and THP-1 foam cells.
Figure 5B:
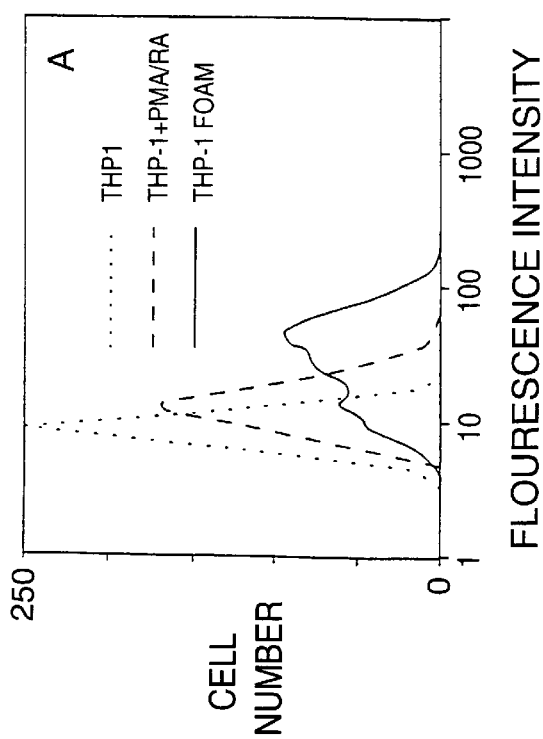
Figure 5C:
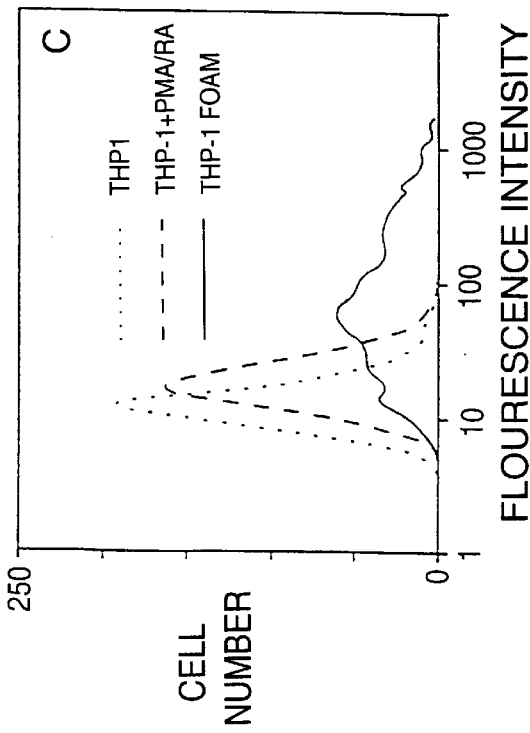

As can be seen in FIGS. 2, 5 (out of the 8 anti-ICAM-3 mAb), 3 (out of 3 CDw50 mAb) together with mAb 3.A9 bind to eluted material of the 3.A9 affinity column. The specificity of this reaction is illustrated by the fact that mAb directed against other major cell surface molecules known to be present on human cells (including HLA class I and CD43 antigen) show no binding. In addition, antibodies against ICAM-1 (84H10, Immunotech Marseille France), ICAM-2 (CBR-IC2/1 disclosed in de Fougerolles et al, 1991) were tested and found to be negative.

In conclusion, the data in examples 3, 4 and 5 indicate that mAb 3.A9 is directed against an epitope of ICAM-3 or of an ICAM-3 related molecule.

Example 6

Monoclonal Antibody 3.A9 is Up-regulated on in vitro THP-1 Foam Cells mAb 3.A9, together with the other CDw50 and anti-ICAM-3 mAb described in example 5, were simultaneously tested by flow cytometry on three different populations of THP-1 cells: (a) THP-1 cells grown in RPMI 1640 medium with 10% FCS (THP-1); (b) THP-1 cells activated for 24 hours with a mixture of $2 \times 10^{-7}$ M PMA and $0.5 \times 10^{-7}$ M RA and then grown for 48 hours under lipid-free conditions (THP-1+PMA/RA); and (c) THP-1 cells activated for 24 hours with a mixture of $2 \times 10^{-7}$ M PMA and $0.5 \times 10^{-7}$ M RA and afterwards cultured for 48 hours in medium with aggregated low density lipoprotein (THP-1 foam). For more details on the preparation of the foam cells, see example 1. For more details on the indirect immunofluorescence staining method, see example 3.

mAb 3.A9 is up-regulated on a considerable percentage (>50%) of in vitro human foam cells (referred to as (c) above). This up-regulation may be variable but appears in all experiments performed until now (FIG. 3). Moreover, as is evident from FIGS. 4 and 5, mAb 3.A9 is the only CDw50 or anti-ICAM-3 mAb that is up-regulated on these foam cells. This would indicate that mAb 3.A9 recognizes a unique epitope on the ICAM-3 antigen, or alternatively, is directed against an ICAM-3 related molecule.

Example 7 mAb 3.A9 inhibits the Allo-antigen Induced Proliferation of Purified T Cells

Isolation and Culture of Monocytes

Buffy coats obtained after cytophoresis of healthy donors were used to prepare monocyte cultures. Mononuclear cell suspensions were obtained after buoyant density centrifugation of buffy coats on LYMPHOPREP™ (Nycomed). The monocyte-enriched, E-negative, fraction was separated from T lymphocytes by standard rosette formation with 2-aminoethylisothio-uronium bromide hydrobromide (Sigma)-treated sheep red blood cells followed by LYMPHOPREP™ sedimentation. Monocytes were further enriched by the cold aggregation technique. The cell suspension was allowed to clump by low speed agitation at 4° C. Cell clumps were separated from the rest of the cells by a short centrifugation run. Monocytes were cultured in RPMI 1640 medium supplemented with 10% FCS, non-essential amino acids, 100 IU/mi penicillin, 100 µg/ml streptomycin, 10 mM L-glutamine and 2 mM sodium pyruvate.

Purification of T Cells

Peripheral blood mononuclear cells (PBMC) were isolated from buffy coat by centrifugation on Lymphoprep™ (Nycomed). T cells were further purified by depletion of monocytes, B cells and NK cells using Lympho-Kwik T (One Lambda, Los Angeles, Calif.) according to the manufacturers protocol.

Mixed Lymphocyte Cultures

T cells ($10^5$/well) were cultured in round-bottom culture plate (Falcon 3072, Becton and Dickinson, Oxnard, Calif.) in presence of autologous or allogeneic monocytes ($10^5$/well). After 3 days of culture, cells were pulsed for 16 hours with 0.5 µCi [3H]thymidine (specific activity of 5 Ci/mMol), after which the cells were harvested by using an automated cell harvester. [3H]Thymidine incorporation was determined with a liquid scintillation counter. Proliferation was assessed in triplicate. In inhibition experiments monocytes were pre-incubated with mAb 84H10 (anti-ICAM-1, Immunotech, Marseille, France) or 3.A9 in complete RPMI medium for 30 minutes at 4° C. before they were dispensed in 96 well round-bottom plates.

Results

Figure 6:
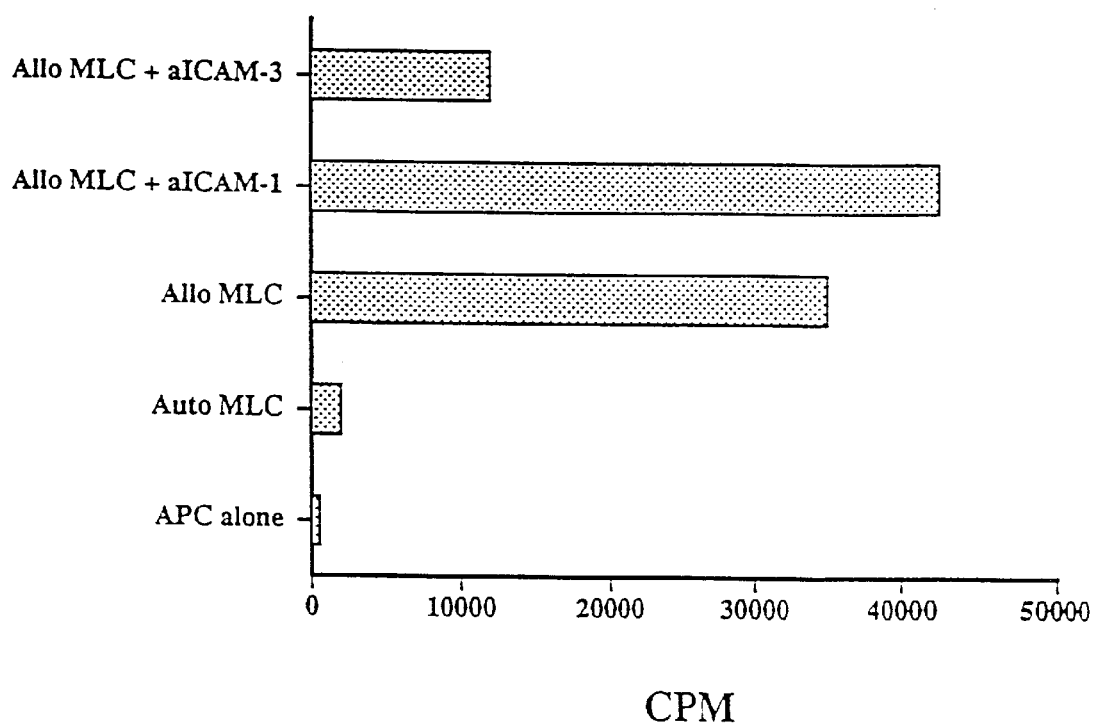
FIG. 6: mAb 3.A9 inhibits alloantigen-induced T cell proliferation. Purified T cells are stimulated in the presence of allogeneic monocytes but not in the presence of autologous monocytes. This alloantigen-induced stimulation can be strongly inhibited by mAb 3.A9 (anti-ICAM-3) but not by mAb 84H10 (anti-ICAM-1). One representative experiment out of two performed.

Monocytes are important antigen presenting cells for antigen-specific T cell activation. Since the antigen recognized by the 3.A9 mAb is constitutively expressed on monocytes, we have addressed the question whether the 3.A9 mAb is able to inhibit the proliferation induced by allogeneic monocytes when these are co-cultured with purified T cells. Monocytes (autologous or allogeneic) and T cells were purified and cultured as described above. Monocytes were pre-incubated with mAb 84H10 (anti-ICAM-1, Immunotech, Marseille, France) or 3.A9 in complete RPMI for 30 minutes at 4° C. before they were added to the 96-well plates for co-culture with the T cells. After 3 days of culture, cells were pulsed for 16 hours with 0.5 µCi [3H]thymidine, after which the cells were harvested by using an automated cell harvester. [3H]Thymidine incorporation was determined with a liquid scintillation counter. FIG. 6 shows that T cells are stimulated to proliferate in the presence of allogeneic monocytes but not in the presence of autologous monocytes. Binding of mAb 3.A9 to its antigen ICAM-3, but not the anti-ICAM-1 mAb 84H10 resulted in a strong inhibition of the activation of T cells, suggesting that the binding of the antigen recognized by mAb 3.A9 to a ligand on T cells is important for its activation. This implies that mAb 3.A9 could be used in vivo to prevent the activation of T cells in clinical situations where T-cell activation is involved in the pathology. In another experiment it was found that mAb 3.A9 not only bound to monocytes, but also to dendritic cells, another class of antigen-presenting cells, and that also proliferation of T cells induced by allogeneic dendritic cells can be inhibited by mAb 3.A9.

Example 8

OKM5 is Another Monoclonal Antibody That is Up-Regulated on THP-1 Foam Cells

We have tested a whole series of antibodies by flow cytometry on three different populations of THP-1: (a) cells grown in RPMI 10% FCS (THP-1); (b) cells activated with a mixture of $2 \times 10^{-7}$ M PMA and $0.5 \times 10^{-7}$ M RA for 24 hours and further grown for 48 hours under lipid-free conditions (THP-1+PMA/RA); and (c) cells activated with a mixture of $2 \times 10^{-7}$ M PMA and $0.5 \times 10^{-7}$ M RA for 24 hours and further incubated with aggregated LDL during 48 hours (THP-1 foam). All necessary experimental details can be found in examples 1 and 3.

mAb OKM5 (Coulter, Hialeah, Fla.) was one of the few markers that showed enhanced binding on THP-1 foam cells in comparison with THP-1+PMA/RA (FIG. 7). This result is in good agreement with in vivo observations in the atherosclerotic plaque. Indeed, immunohistochemical studies of van der Wal et al. (1992) revealed the presence of OKM5 positive cells in the centre of the plaque, which was correlated with lipid accumulation and lysosomal activity. mAb OKM5 has been clustered in CD36. There is evidence that the CD36 antigen serves as a receptor for extracellular matrix components such as thrombospondin (Asch et al., 1987) and collagen (Tandon et al., 1989). However, it has recently been published that the CD36 molecule also functions as a macrophage receptor for oxidized LDL (Endemann et al., 1993). The results in this example thus further emphasize the resemblance of our in vitro foam cell model to the in vivo atherosclerotic plaque situation.

TABLE 1

Cholesterol accumulation in THP-1 and K-562 cells

| Inducer | LDL | | acetyl-LDL | | aggregated LDL | |
| --- | --- | --- | --- | --- | --- | --- |
| | TC | % CE | TC | % CE | TC | % CE |
| THP-1 | | | | | | |
| — | 21.5 ± 3.6 | 16.0 ± 1.9 | 15.0 ± 1.4 | 10.7 ± 5.2 | 22.3 ± 1.7 | 17.3 ± 8.5 |
| PMA 24 h | 27.0 ± 1.2 | <5 | 45.3 ± 3.5 | <5 | 30.7 ± 5.8 | 9.5 ± 5.5 |
| PMA 72 h | 25.9 ± 11.8 | 10.8 ± 12.3 | 27.3 ± 1.7 | 11.3 ± 9.8 | 50.9 ± 5.1 | 10.9 ± 3.7 |
| PMA/RA 24 h | 32.5 ± 3.5 | <5 | 42.0 ± 5.2 | <5 | 139.0 ± 36.4 | 46.3 ± 5.7 |
| K-562 | | | | | | |
| — | 30.5 ± 6.9 | 42.6 ± 5.7 | 18.7 ± 3.5 | 26.1 ± 8.0 | 32.3 ± 5.8 | 32.7 ± 5.2 |
| PMA 24 h | 42.4 ± 3.8 | 37.4 ± 4.2 | 37.4 ± 2.8 | 33.0 ± 4.3 | 39.8 ± 9.5 | 31.9 ± 5.0 |
| PMA/RA 24 h | ND | | ND | | 29.4 ± 6.5 | 26.5 ± 6.2 |

TC: total cholesterol expressed as µg/mg protein
% CE: % cholesteryl esters

TABLE 2

Reactivity of mAb 3.A9 with human B, T, myeloid and erythroid cell lines and with normal blood cells

| Cell type | % positive[a] | mean fluorescence intensity[b] | |
|---|---|---|---|
| | | mAb 3.A9 | mAb 1.24[c] |
| Myeloid/monocytic cell lines | | | |
| KG-1 | 97 | 312 | 7 |
| KG-1a | 96 | 362 | 11 |
| HL-60 | 86 | 25 | 4 |
| U-937 | 91 | 57 | 4 |
| THP-1 | 81 | 13 | 3 |
| Erythroleukemic cell lines | | | |
| K-562 | 3 | 12 | 9 |
| HEL | 73 | 31 | 8 |
| T cell lines | | | |
| CCRF-CEM | 97 | 105 | 3 |
| Jurkat | 93 | 59 | 4 |
| MOLT-4 | 97 | 69 | 4 |
| HuT 78 | 97 | 268 | 8 |
| B cell lines | | | |
| Daudi | 0 | 4 | 4 |
| Raji | 0 | 4 | 4 |
| CCRF-SB | 97 | 87 | 4 |
| Normal peripheral blood | | | |
| Lymphocytes | 91 | 296 | 7 |
| Neutrophils | 97 | 285 | 12 |
| Monocytes | 97 | 476 | 21 |
| Erythrocytes | 0 | 3 | 2 |
| Platelets | 0 | 4 | 3 |

[a]The % positive cells is determined as follows. A marker is set so that using the 1.24 negative control mAb 3% of the cells are brighter than the marker. The % of cells positive with mAb 3.A9 is then the % brighter than this marker minus 3%.
[b]Mean fluorescence intensity (on a four decade log scale) obtained with mAb 3.A9 and with isotype-specific control mAb 1.24 are given.
[c]mAb 1.24 is directed against a rabbit leukocyte surface antigen (De Smet et al., 1983) and does not cross-react with human cells. It was used as a negative control in the flow cytometry studies.

REFERENCES

Asch A, Barnwell J, Silverstein R, Nachman R (1987) Isolation of the thrombospondin membrane receptor. J. Clin. Invest. 79: 1054–1061

Auwerx J, Deeb S, Brunzell J, Peng R, Chait A (1988) Transcriptional activation of the lipoprotein lipase and apolipoprotein E genes accompanies differentiation in some human macrophage-like cell lines. Biochem. 27: 2651–2655

Basu S, Brown M, Ho Y, Goldstein J (1979) Degradation of low density lipoprotein-dextran sulfate complexes associated with deposition of cholesteryl esters in mouse macrophages. J. Biol. Chem. 254: 7141–7146

Bowyer D, Mitchinson M (1989) The role of macrophages in atherosclerosis. In: Human monocytes. Ed. Zembala M and Asherson G, Academic Press Limited: 437–458

Carrera A, Rincon M, Sanchez-Madrid F, Lopez-Botet M, de Landazuri M (1988) Triggering of co-mitogenic signals in T cell proliferation by anti-LFA-1 (CD18, CD11a), LFA-3, and CD7 monoclonal antibodies. J. Immunol. 141: 1919–1924

Davignon D, Martz E, Reynolds T, Kurzinger K, Springer T (1981) Lymphocyte function-associated antigen 1 (LFA-1): a surface antigen distinct from Lyt-2, 3 that participates in T lymphocyte-mediated killing. Proc-Natl-Acad-Sci-U.S.A. 78: 4535–4539.

de Fougerolles A, Stacker S, Schwarting R, Springer T (1991) Characterization of ICAM-2 and evidence for a third counter-receptor for LFA-1. J. Exp. Med. 174: 253–267 de Fougerolles A, Springer T (1992) Intercellular adhesion molecule 3, a third adhesion counter-receptor for lymphocyte function-associated molecule 1 on resting lymphocytes. J. Exp. Med. 175: 185–190 de Fougerolles A, Klickstein L, Springer T (1993) Cloning and expression of intercellular adhesion molecule 3 reveals strong homology to other immunoglobulin family counter-receptors for lymphocyte function-associated antigen 1. J. Exp. Med. 177: 1187–1192

De Smet W, Vaeck M, Smet E, Brys L, Hamers R (1983) Rabbit leukocyte surface antigens defined by monoclonal antibodies. Eur. J. Immunol. 13: 919–928

De Smet W, Walter H, Van Hove L (1993) A new CD43 monoclonal antibody induces homotypic aggregation of human leucocytes through a CD11a/CD18-dependent and -independent mechanism. Immunology 79: 46–54

Dougherty G, McBride W (1989) Monocyte differentiation in vitro. In: Human monocytes. Ed. Zembala M and Asherson G, Academic Press Limited: 437–458

Dustin M, Staunton D, Springer T (1988) Supergene families meet in the immune system. Immunol. Today 9: 213–215

Endemann G, Stanton L, Madden K, Bryant C, White R, Protter A (1993) CD36 is a receptor for oxidized low density lipoprotein. J. Biol. Chem. 268: 11811–11816

Fawcett J, Holness C, Needham L, Turley H, Gatter K, Mason D, Simmons D (1992) Molecular cloning of ICAM-3, a third ligand for LFA-1, constitutively expressed on resting leukocytes. Nature 360: 481–484

Fisher A, Durandy A, Sterkers G, Griscelli C (1986) Role of het LFA-1 molecule in cellular interactions required for antibody production in humans. J Immunol 136: 3198–3203.

Forte T, Nordhausen R (1986) Electron microscopy of negatively stained lipoproteins. Methods Enzym. 128: 442–457

Gabizon A, Dagan A, Goren D, Barenholz Y, Fuks Z (1982) Liposomes as in vivo carriers of adriamycin: reduced cardiac uptake and preserved antitumor activity in mice. Cancer Res 42: 4734–4739.

Gilks W (1990) Leucocyte typing database IV. Oxford University Press, Oxford

Grossman H (1986) Clinical applications of monoclonal antibody technology. Urol Clin North Am 13: 465–474.

Hadam M (1989) Cluster report: CDw50. In: Leucocyte Typing IV. White cell differentiation antigens. Eds. Knapp W, D÷rken B, Gilks W, Rieber E, Schmidt R, Stein H, von dem Borne A. p 667–670. Oxford University Press, Oxford Haley N, Shio H, Fowler S (1977) Characterization of lipid-laden aortic cells from cholesterol-fed rabbits. I. Resolution of aortic cell populations by metrizamide density gradient centrifugation. Lab. Invest 37: 287–296.

Hara H, Tanishita H, Yokoyama S, Tajima S, Yamamoto A (1987) induction of acetylated low density lipoprotein receptor and suppression of low density lipoprotein receptor on the cells of human monocytic leukemia cell line (THP-1 cell). Biochem. Biophys. Res. Commun. 146: 802–808

Haskard D, Cavender D, Beatty P, Springer T, Ziff M (1986) T lymphocyte afhesion to endothelial cells: mechanisms demonstrated bij anti-LFA-1 monoclonal antibodies. J Immunol 137: 2901–2906.

Juan M, Vilella R, Mila J, Yague J, Miralles A, Campbell K, Friedrich R, Cambier J, Vives J, de Fougerolles A, Springer T (1993) CDw50 and ICAM-3: two names for the same molecule. Eur. J. Immunol. 23: 1508–1512

Khaw B, Fallon F, Strauss H, Haber E (1980) Myocardial infarct imaging of antibodies to canine cardiac myosin with indium-111-diethylenetriamine pentaacetic acid. Science 209: 295–297.

Khoo J, Miller E, McLoughlin P, Steinberg D (1988) Enhanced macrophage uptake of LDL after self-aggregation. Arteriosclerosis 8: 348–358

Knauf M, Bell DP, Hirtzer P, Luo Z, Young J, Katre N (1988) Relationship of effective molecular size to systemic clearance in rate of recombinant interleukin-2 chemically modified with water-soluble polymers. J Biol Chem.263: 15064–15070.

Krensky A, Robbins E, Springer T, Burakoff S (1984) LFA-1, LFA-2 and LFA-3 antigens are involved in CTL-target conjugation. J Immunol 132: 2180–2182.

Kohl S, Springer T, Schmalstieg F, Loo L, Anderson D (1984) Defective natural killer cytotoxicity and polymorphonuclear leukocyte antibodt-dependent cellular cytotoxicity in patients with LFA-1/OKM-1 deficiency. J Immunol 133: 2972–2978.

Laemmli U (1970) Cleavage of structural proteins during the assembly of the head of bacteriophage T4. Nature 227: 680–685

Larson R, Springer T (1990) Structure and function of leukocyte integrins. Immunol. Rev. 114: 181–217

Lyons A, Ashman L (1989) Monocyte cell lines. In: Human monocytes. Ed. Zembala M and Asherson G, Academic Press Limited: 437–458

Mach J-P, PΦlegrin A, Buchegger F (1991) Imaging and therapy with monoclonal antibodies in non-hematopoietic tumors. Current Opinion Immunol. 3: 685–693

Menju M, Tajima S, Yamamoto A (1989) Expression of the apolipoprotein E gene in a human macrophage-like cell line, THP-1. J. Biochem. 106: 505–510

Perkins A, Whalley D, Ballantyne K, Pimm M (1988) Gamma camera emission tomography using radiolabelled antibodies. Eur J Nucl Med 14: 45–49

Peters S, Bielfeldt T, Meldal M, Bock K, Paulsen H (1991) Multiple column solid phase glycopeptide synthesis. Tetrahedron Letters 32: 5067–5070

Poznansky M, Juliano R (1984) Biological approaches to the controlled delivery of drugs: a critical review. Pharmacol Rev.36: 277–336.

Ross R (1986) The pathogenesis of atherosclerosis—an update. New Eng. J. Med. 314: 488–500

Rothlein R, Springer T (1986) The requirement for lymphocyte function-associated antigen 1 in homotypic leukocyte adhesion stimulated by phorbol ester. J Exp Med 163: 1132–1149.

Sanchez-Madrid F, Krensky A, Ware C, Robbins E, Strominger J, Burakoff S, Springer T (1982) Three distinct antigens associated with human T lymphocyte-mediated cytolisis: LFA-1, LFA-2 and LFA-3. Proc. Natl. Acad. Sci. U.S.A. 79: 7489–7493

Snow J, McCloskey H, Glick J, Rothblat G, Phillips M (1988) Physical state of cholesteryl esters deposited in cultured macrophages. Biochem., 27: 3640–3646

Snow J, Glick J, Phillips M (1992) The phase behavior of cholesteryl esters in intracellular inclusions. J. Biol. Chem. 267: 18564–18572

Springer T (1990) Adhesion receptors of the immune system. Nature 346: 425–434

St. Clair R (1986) Pathogenesis of the atherosclerotic lesion: current concepts of cellular and biochemical events. In: Recent advances in arterial diseases: Atherosclerosis, hypertension, and vasospasm. Ed. A. Liss, Inc. 1–29 (1986)

Strassmann G, Springer T, Somers S, Adams D (1986) Mechanisms of tumor cell capture by activated macrophages: evidence for involvement of lymphocyte function-associated (LFA-1) antigen.

Suits A, Chait A, Aviram M, Heinecke J (1989) Phagocytosis of aggregated lipoprotein by macrophages: low density lipoprotein receptor-independent foam cell formation. Proc. Natl. Acad. Sci. U.S.A. 86: 2713–2717

Szoka F Jr, Papahadjopoulos D (1980) Comparative properties and methods of preparation of lipid vesicles (liposomes). Annu-Rev-Biophys-Bioeng 9: 467–508.

Tabas I, Weiland D, Tall A (1985) Unmodified low density lipoprotein causes cholesteryl ester accumulation in J774 macrophages. Proc. Natl. Acad. Sci. U.S.A. 82: 416–420

Tajima S, Hayashi R, Tsuchiya S, Miyabe Y, Yamamoto A (1985) Cells of a human monocytic leukemia cell line (THP-1) synthesize and secrete apolipoprotein E and lipoprotein lipase. Biochem. Biophys. Res. Commun. 126: 526–531

Tandon N, Kralisz U, Jamieson G (1989) Identification of glycoprotein IV (CD36) as a primary receptor for platelet-collagen adhesion. J. Biol. Chem. 264: 7576–7583

Tsuchiya S, Yamabe M, Yamaguchi Y, Kobayashi Y, Konno T, Tada K (1980) Establishment and characterization of a human acute monocytic leukemia cell line (THP-1). Int. J. Cancer 26: 171–176

Tsuchiya S, Kobayashi Y, Goto Y, Okumura H, Nakae S, Konno T, Tada K (1982) Induction of maturation in cultured human monocytic leukemia cells by a phorbol diester. Cancer Res. 42: 1530–1536

Unger E, Totty W, Neufeld D, Otsuka F, Murphy W, Welch M, Connett J, Philpott G (1985) Magnetic resonance imaging using gadolinium labelled monoclonal antibody. Invest Radiol 20: 693–700.

van der Wal A, Das P, Tigges A, Becker A (1992) Macrophage differentiation in atherosclerosis. An in situ immunohistochemical analysis in humans. Am. J. Pathol. 141: 161–168

Vazeux R, Hoffman P, Tomita J, Dickinson E, Jasman R, St. John T, Gallatin W (1992) Cloning and characterization of a new intercellular adhesion molecule ICAM-R. Nature 360: 485–488

Vercaemst R, Rosseneu M, Van Biervliet J (1983) Separation and quantitation of plasma lipoproteins by high-performance liquid chromatography. J. Chromatogr. 276: 174–181

Vercaemst R, Union A, Rosseneu M (1989) Separation and quantitation of free cholesterol and cholesteryl esters in a macrophage cell line by high-performance liquid chromatography. J. Chromatogr. 494: 43–52

Via D, Plant A, Craig I, Gotto A, Smith L (1985) Metabolism of normal and modified low-density lipoproteins by macrophage cell lines of murine and human origin. Biochem. Biophys. Acta 833: 417–428

Vilella R, Mila J, Lozano F, Alberola-Ila J, Places L, Vives I (1990) Involvement of the CDw50 molecule in allorecognition. Tissue Antigens 36: 203–210

Wawryk S, Novotny J, Wicks I, Wilkinson D, Maher D, Salvaris E, Welch K, Fecondo J, Boyd A (1989) The role of the LFA-1/ICAM-1 ineraction in human leukocyte homing and adhesion. Immunol. Rev. 108: 135–161

Yamamoto A, Hara H, Takaichi S, Wakasugi J, Tomikawa M (1988) Effect of probucol on macrophages, leading to regression of xanthomas and atheromatous vascular lesions. Am. J. Cardiol. 62: 31B–36B

We claim:

1. A method for producing a monoclonal antibody showing an increased binding to THP-1 foam cells compared to its binding to THP-1 cells treated for 24 hours with a mixture containing $2\times10^{-7}$ M PMA and $0.5\times10^{-7}$ M retinoic acid:

said monoclonal antibody recognizing an antigen binding to the monoclonal antibody 3.A9F5E1 produced by a hybridoma cell line deposited in the ECACC under No. 93102638 on Oct. 26, 1993; said THP-1 foam cells having been deposited at the ATCC under No. TIB-202 on Oct. 1, 1983, said method comprising the steps of:
 (a) immunizing an animal with KG-1a cells,
 (b) fusing the spleen cells of said animal with myeloma cells to form antibody secreting hybridoma cells,
 (c) screening the hybridoma cells for production of monoclonal antibodies directed against KG-1a cells, and
 (d) screening the hybridoma cells scoring positive in step (c) for production of a monoclonal antibody which shown an increased binding to THP-1 foam cells compared to its binding to THP-1 cells treated for 24 hours with a mixture containing $2\times10^{-7}$ M PMA and $0.5\times10^{-7}$ retinoic acid,
 (e) culturing the selected hybridoma according to step (d) in a culture medium,
 (f) recovering the monoclonal antibodies secreted by the selected hybridomas cultured as in (e), or alternatively,
 (g) implanting the selected hybridomas as in (e) into the peritoneum of a mouse and, when ascites has been produced by the animal, recovering the monoclonal antibodies, said KG-1a cells having been deposited on Dec. 12, 1984, at ATCC CCL 246.1 with the ATCC.

2. A method for producing a hybridoma cell line comprising the steps of:
 (a) immunizing an animal with KG-1a cells,
 (b) fusing the spleen cells of said animal with myeloma cells to form antibody secreting hybridoma cells,
 (c) screening the hybridoma cells for production of monoclonal antibodies directed against KG-1a cells, and
 (d) screening the hybridoma cells scoring positive in step (c) for production of a monoclonal antibody which shows an increased binding to THP-1 foam cells compared to its binding to THP-1 cells treated for 24 hours with a mixture containing $2\times10^{-7}$ M PMA and $0.5\times10^{-7}$ retinoic acid, said KG-1a cells having been deposited on Dec. 12, 1984, as ATCC CCL 246.1 with the ATCC.

* * * * *